US006992078B2

(12) United States Patent
Lin et al.

(10) Patent No.: US 6,992,078 B2
(45) Date of Patent: Jan. 31, 2006

(54) PLANT EXTRACTS AND ALKALOIDS HAVING ANTITUSSIVE ACTIVITY

(75) Inventors: Ge Lin, Hong Kong (CN); Hoi Sing Chung, Hong Kong (CN); Po Ming Hon, Hong Kong (CN); Hui Dong, Hong Kong (CN); Paul P. H. But, Hong Kong (CN)

(73) Assignee: The Chinese University of Hong Kong, Shatin (HK)

( * ) Notice: Subject to any disclaimer, the term of this patent is extended or adjusted under 35 U.S.C. 154(b) by 340 days.

(21) Appl. No.: 10/132,865

(22) Filed: Apr. 24, 2002

(65) Prior Publication Data

US 2003/0229071 A1 Dec. 11, 2003

(51) Int. Cl.
  *A61P 11/14* (2006.01)
  *A61K 31/55* (2006.01)
  *C07D 223/00* (2006.01)
  *C07D 223/14* (2006.01)

(52) U.S. Cl. .................. 514/214.01; 540/581; 540/586
(58) Field of Classification Search ............ 514/214.01; 540/581, 586
See application file for complete search history.

(56) References Cited

PUBLICATIONS

CAPLUS printout of Uyeo et al., Structure of Stenine, a New Alkaloid in Stemona Tuberosa, Chemical & Pharmaceutical Bulletin, vol. 15, No. 6, pp. 768–770, 1967.*
CAPLUS printout of Pfeifer et al., Alkaloids of Vietnamese Stemona Tuberosa, Pharmazie, vol. 23, No. 6, pp. 342–343, 1968.*
CAPLUS printout of Ye et al., Alkaloids from Tuberosa, Phytochemistry, vol. 37, No. 4, pp. 1201–1203, 1994.*
CAPLUS printout of Pham et al., Alkaloids from Stemona Collinsae, Journal of Asian Natural Products Research, vol. 4, No. 2, pp. 81–85, 2002.*
Changying, Zou et al.; "New alkaloids from the roots of Stemona japonica Miq."; *Journal of Chinese Pharmaceutical Sciences*; 1999; pp. 185–190; vol. 8, No. 4.
Dao, C. Ngoan et al.; "Tuberostemonine L–G"; *Acta Cryst.*; 1994; pp. 1612–1615; vol. C50; International Union of Crystallography.
Götz, M. and G. M. Strunz; "Tuberostemonine and related compounds: the chemistry of the Stemona alkaloids"; *Alkaloids (K. Wiesner, ed.)*; 1973; pp. 143–160; University Park Press; Baltimore.

Liu, Shiwang et al.; "New alkaloids from roots of Stemona tuberosa (Translation of title)"; *Acta Pharmaceutica Sinica*; 1999; pp. 372–375; vol. 34, No. 5 (In Chinese).

Pham, Huu Dien et al.; "Alkaloids from Vietnamese Stemona tuberosa Lour(Stemonaceae) Part 1; Neotuberostemonine and bisdehydroneotuerostemonine (Translation of title)"; *Tao Chi Hoa Hoc*; 2000; pp. 64–67; vol. 38, No. 1 [In Vietnamese].

Pilli, Ronaldo Aloise and Maria Da Conceição Ferreira de Oliveira; "Recent progress in the chemistry of the Stemonaalkaloids"; *Nat. Prod. Rep.*; 2000; pp. 117–127; vol. 17; The Royal Society of Chemistry .

Qin, Guo–wei and Ren–sheng Xu; "Recent advances on bioactive natural products from Chinese medicinal plants"; *Med. Res. Rev.*; 1998; pp. 375–382; vol. 18, No. 6; John Wiley & Sons.

Shinozaki, H. and M. Ishida; "Inhibitory actions of tuberostemonine on the excitatory transmission at the crayfish neuromuscular junction"; *Brain Research*; 1985; pp. 33–40; vol. 334; Elsevier Science Publishers B.V.

Wen–Han, Lin, et al.; "Chemical studies on new Stemonaalkaloids, IV. Studies on new alkaloids from Stemona tuberosa"; *Journal of Natural Products*; 1992; pp. 571–576; vol. 55, No. 5.

WenHan, Lin and Fu Hongzheng; "Three new alkaloids from the roots of Stemona tuberosa Lour"; *Journal of Chinses Pharmaceutical Sciences*; 1999; pp. 1–7; vol. 8, No. 1.

* cited by examiner

*Primary Examiner*—Brenda Coleman
(74) *Attorney, Agent, or Firm*—Townsend and Townsend and Crew LLP

(57) ABSTRACT

The present invention provides plant extracts, isolated alkaloids, synthetic alkaloids and compositions having antitussive activity. In some preferred embodiments, the plant extracts and the isolated alkaloids are from a plant of a genus in the family Stemonaceae. In other preferred embodiments, the plant extracts and the isolated alkaloids are from a plant of the genus Stemona, Croomia, or Stichoneuron. In especially preferred embodiments, the plant extracts and the isolated alkaloids are from the plant Stemona tuberosa. The present invention further provides methods for isolating such plant extracts and alkaloids. In addition, the present invention provides methods for reducing or suppressing coughing by administering plant extracts, alkaloids and compositions having antitussive activity.

32 Claims, 14 Drawing Sheets

Compound B

Compound C

Compound D

Compound E

Compound F

Compound G

Compound H

Compound A

PLANT EXTRACTS AND ALKALOIDS HAVING ANTITUSSIVE ACTIVITY

FIELD OF THE INVENTION

This invention pertains to the field of plant extracts, isolated plant alkaloids, and synthetic alkaloids that have antitussive activity and which are useful as pharmaceutical agents for reducing or suppressing coughing.

BACKGROUND OF THE INVENTION

Coughing provides a means for clearing the tracheal and bronchial trees of a accumulated secretions and/or foreign bodies. The mechanism of coughing is initiated by an appropriate stimulus which elicits a deep inspiration, followed by closure of the epiglottis and relaxation of the diaphragm. Thereafter, a sharp muscle contraction against the closed epiglottis occurs, thereby, producing increased pressure in the intra-thoracic and intra-airway passages. The positive intra-thoracic pressure causes a narrowing of the trachea due to enfolding of its compliant posterior membrane and opens the epiglottis. When the epiglottis opens, the combination of the large pressure differential between the thoracic cavity and the atmosphere, coupled with the narrowing of the trachea, produces a massively increased rate of air flow through the trachea. The force created by this increased rate of air flow can effect the clearance of expectorate mucus and foreign materials from the airway.

Coughing is caused by a variety of stimuli, including physiological, mechanical, or chemical stimuli. For example, coughing is produced by inflammatory mechanisms, mechanical disorders, and chemical and thermal stimulation. Also for example, inflammatory stimuli can be initiated by edema of the mucosal membranes. The edema, in turn, can be from any etiology, for example, bacterial or viral infection, the common cold, or excessive cigarette smoking. Inflammatory stimuli may also be elicited by irritation from exudative processes such as post-nasal drip and gastric reflux. Such stimuli may arise in the airways, for example as in laryngitis, bronchitis, pneumonia or an abscess in the lungs.

Further, mechanical stimuli, for example the inhalation of particulate matter, can cause coughing. Other mechanical disorders which result in compression of the air passages or increased pressure upon any area of the respiratory system may result in coughing. Such mechanical difficulties may arise from intra-mural or extra-mural etiologies. For example, extra-mural causes of coughing include extra-mural pressure caused by an aortic aneurysm, granulomas, pulmonary neoplasms, mediastinal tumors, and the like. Intra-mural lesions, such as bronchiogenic carcinoma, bronchial adenoma, the presence of foreign bodies or bronchial asthma also result in coughing. Decreased pliancy of the respiratory membranes may also result in chronic coughing, as in the case of patients suffering from cystic fibrosis.

Chemical stimuli, for example the inhalation of irritant gases (e.g., cigarette smoke or chemical fumes) may also elicit coughing. Other chemical entities result in coughing due to their reactive effect upon the respiratory system itself or on the balance and uptake of respiratory gases. Additionally, many chemical agents induce coughing due to their reaction with enzymes involved in the respiratory process. Lastly, thermal stimuli, such as the inhalation of either very hot or cold air, may also result in coughing.

In some disease states, a persistent cough can be the only or primary symptom. For example, patients suffering from bronchial asthma can result in incessant coughing. Moreover, in some medical conditions, for example, asthma, the cough mechanism itself may further aggravate the patient's condition. Asthma is a condition marked by recurrent attacks of paroxysmal dyspnea with wheezing, which is due to spasmodic contraction of the bronchi. The condition is caused by various etiologies. In some cases, asthma is the result of an allergic reaction. A variety of factors including vigorous exercise, chemical or particulate irritation, or even psychological stress can stimulate or provoke coughing. Moreover, the violent contractions of the thoracic cavity which accompany coughing further aggravates already irritated respiratory membranes. A review of the physiology of coughing is presented by Karlsson et al., *Pulmonary Pharmacology and Therapeutics* (1999) 12:215–238.

A variety of antitussive drugs have been developed for the treatment of coughing, for example, morphine-like compounds and compounds that act on opioid receptors. However, these compounds have adverse side effects. For example, the use of morphine-like compounds are known to result in addiction, respiratory suppression, and inhibitory action of smooth muscle contraction (e.g., resulting in constipation), and psychotomimetics. In particular, codeine is known to be highly addictive and dextromethorphan is known to induce hallucinations, delusions, or other symptoms of a psychosis. Moreover, drugs having strong antitussive activity, for example codeine and dextromethorphan, are known to adversely act on the central nervous system. Further, drugs that act on opioid receptors are known to adversely effect urination (Leander et al. *Pharmacol. Exp. Ther.*, 227:35 (1983). A review of antitussive drugs is presented by Hey et al., *Annual Reports in Medicinal Chemistry* 35:53–62 (2000) and Bolser, *Pulmonary Pharmacology* 9:357–364 (1996).

A variety of drugs are available for the treatment of coughing. However, the number of safe and effective antitussive agents devoid of unwanted side effects, for example, sedation and addiction, is limited. In view of the serious adverse side effects of the drugs used to treat coughing, there is a need for antitussive drugs that are free of such side effects and are effective in reducing or suppressing coughing. The present invention fulfills these and other needs.

SUMMARY OF THE INVENTION

The present invention provides, inter alia, antitussive compounds that are free of side-effects and are effective in reducing or suppressing coughing. In one aspect, the antitussive compounds are plant extracts or their derivatives such as from the family *Stemonaceae*.

As such, in one embodiment, the present invention provides a compound having Formula I:

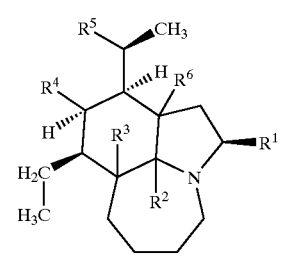

In Formula I, $R^1$ is selected from a hydrogen and an α(S)-methyl-γ(S)-butyroylactonyl; $R^2$ is selected from β-oriented hydrogen and an α-oriented hydrogen; $R^3$ is selected from a β-oriented hydrogen and an α-oriented hydrogen; R⁴ is hydroxyl; R⁵ is selected from a hydroxymethyl and a carboxyl. In an alternative embodiment, R⁴ and R⁵ together with the carbons to which they are attached, join to form a substituted γ(S)-butyroylactonyl or substituted furane ring; and R⁶ is selected from a β-oriented hydrogen and an α-oriented hydrogen. In another embodiment, R⁴ and R⁵ together with the carbons to which they are attached, join to form a substituted γ(S)-butyroylactonyl and R² and R⁶ are both absent and form a pyrrole ring, provided however, that when R¹ is α(S)-methyl-γ(R)-butyroylactonyl, R³ is an α-oriented hydrogen.

In another embodiment, the present invention provides a pharmaceutical composition, the composition comprising a compound having Formula I:

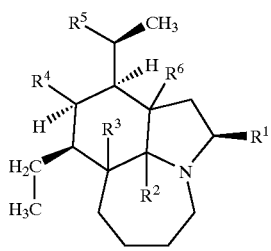

R¹ is selected from a hydrogen and an α(S)-methyl-γ(S)-butyroylactonyl; R² is selected from a β-oriented hydrogen and an α-oriented hydrogen; R³ is selected from a β-oriented hydrogen and an α-oriented hydrogen; R⁴ is hydroxyl; R⁵ is selected from a hydroxymethyl and a carboxyl, or alternatively, R⁴ and R⁵ together with the carbons to which they are attached, join to form a substituted γ(S)-butyroylactonyl or substituted furane ring; and R⁶ is selected from a β-oriented hydrogen and an α-oriented hydrogen. In another embodiment, R⁴ and R⁵ together with the carbons to which they are attached, join to form a substituted γ(S)-butyroylactonyl and R² and R⁶ are both absent and form a pyrrole ring, provided however, that when R¹ is α(S)-methyl-γ(R)-butyroylactonyl, R³ is an α-oriented hydrogen, and a pharmaceutically acceptable carrier.

In another embodiment, the present invention provides a method for reducing coughing in a subject, the method comprising: administering a pharmaceutically effective amount of a compound having Formula I:

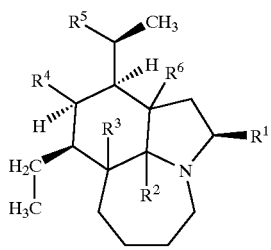

wherein: R¹ is selected from a hydrogen and an α(S)-methyl-γ(S)-butyroylactonyl; R² is selected from a β-oriented hydrogen and an α-oriented hydrogen; R³ is selected from β-oriented hydrogen and an α-oriented hydrogen; R⁴ is hydroxyl; R⁵ is selected from a hydroxymethyl and a carboxyl. In an alternative embodiment, R⁴ and R⁵ together with the carbons to which they are attached, join to form a substituted γ(S)-butyroylactonyl or substituted furane ring; and R⁶ is selected from a β-oriented hydrogen and an α-oriented hydrogen. In another embodiment, R⁴ and R⁵ together with the carbons to which they are attached, join to form a substituted γ(S)-butyroylactonyl and R² and R⁶ are both absent and form a pyrrole ring, provided however, that when R¹ is α(S)-methyl-γ(R)-butyroylactonyl, R³ is an α-oriented hydrogen, thereby reducing coughing in a subject.

In yet another embodiment, the present invention provides a *Stemonaceae* family plant extract having antitussive activity, wherein the *Stemonaceae* family plant extract inhibits a cough in a subject. In certain aspects, the genus belonging to the *Stemonaceae* family is selected from *Stemona*, *Croomia*, or *Stichoneuron*. Preferably, the species of the *Stemona* or *Croomia* genus is selected from *S. collinsae*, *S. japonica*, *S. mairei*, *S. parviflora*, *S. sessilifolia*, *S. tuberosa*, *C. japonica*, and *C. heterosepala* wherein *C.* represents *Croomia*. In one preferred embodiment, the *Stemona* species is *Stemona tuberosa*. The plant extract can be an aqueous extract or a total alkaloid extract.

In other embodiments, the present invention provides a pharmaceutical composition, comprising: a *Stemonaceae* family plant extract having antitussive activity, wherein the *Stemonaceae* family plant extract inhibits a cough in a subject.

In still yet another embodiment, the present invention provides a method for reducing coughing in a subject, comprising: administering a pharmaceutically effective amount of a *Stemonaceae* family plant extract having antitussive activity, wherein the *Stemonaceae* family plant extract inhibits a cough in a subject.

In yet another embodiment, the present invention provides a method for preparing a total alkaloid extract having antitussive activity from a *Stemonaceae* family plant, the method comprising: (a) contacting a *Stemonaceae* family plant sample with an alcohol to form a liquor; (b) evaporating the alcohol in the liquor to form a syrup; (c) adjusting the syrup to an acid pH to form a supernatant fraction; (d) adjusting the supernatant fraction to a basic pH, and then extracting with an organic solvent to form an organic solution; and (e) evaporating the organic solvent to dryness to form a total alkaloid extract having antitussive activity.

In still yet another embodiment, the present invention further provides a method for preparing four *Stemona* alkaloids having antitussive activities from a total alkaloid extract as mentioned above, the method further comprising separating, purifying and crystallizing the total alkaloid extract, to form four *Stemona* alkaloids having antitussive activity. The four *Stemona* alkaloids can be separated using conventional chromatographic techniques.

In still yet another embodiment, the present invention provides a method for preparing an aqueous extract having antitussive activity from a *Stemonaceae* family plant, the method comprising: (a) contacting a *Stemonaceae* family plant sample with an aqueous solvent to form a liquor; and (b) evaporating the liquor to dryness to form an aqueous extract having antitussive activity.

These and other embodiments will become more apparent when read with the detailed description and drawings which follow.

BRIEF DESCRIPTION OF THE DRAWINGS

FIG. 1 shows the chemical structural formulae of eight related *Stemona* alkaloids.

FIG. 2 illustrates the antitussive effects of the aqueous extract derived from *Stemona tuberosa*.

FIG. 3 illustrates the antitussive effects of the total alkaloid extract derived from *Stemona tuberosa*.

FIG. 4 illustrates the antitussive effects of neotuberostemonine (compound A).

FIG. 5 illustrates the antitussive effects of compounds A, B, C, and D in animals.

Table 1 shows chemical structural formulae of compounds A, B, C, D, E, F, G and H.

Table 2 shows crystallographic data, parameters and refinements of compounds A, B, C, D, E and F.

Table 3 shows structure-antitussive activity relationship of five naturally occurring *Stemona* alkaloids. Data are expressed as mean ±SEM. *P<0.05 and ***P<0.001 compared with the vehicle control.

Table 4 shows structure-antitussive activity relationship of three synthetic *Stemona* alkaloids and compound D. Data are expressed as mean ±SEM. *P<0.05 and ***P<0.001 compared with the vehicle control.

Table 5 shows results of effects of different antagonists on the antitussive activity produced by compound A. Data are expressed as mean ±SEM.

Table 6 shows results of radiolabeled ligand binding assays of compound A. ± indicates slight but not significant inhibition on ligand binding.

DETAILED DESCRIPTION OF THE INVENTION

I. General

The present invention provides antitussive compounds such as *Stemona* alkaloids, plant extracts, compositions, methods of preparation and methods of using the same. Advantageously, the antitussive compounds, plant extracts, and compositions are efficacious to treat coughing and are free of side-effects. The antitussive compounds, plant extracts, and compositions effectively reduce and or suppress coughing. As used herein, the term "antitussive activity," refers to the reduction or suppression of coughing.

A. Compounds

The present invention provides antitussive compounds, such as *Stemona* alkaloids useful in reducing or suppressing coughing. As will be apparent to one of skill in the art, certain compounds of the present invention possess asymmetric carbon atoms (chiral centers) or double bonds; the racemates, diastereomers, enantiomers, geometric isomers and individual isomers are all intended to be encompassed within the scope of the present invention.

Figure 1A:
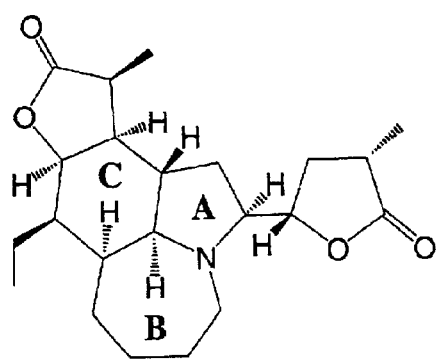
FIG. 1A shows the chemical structural formulae of compounds B, C, D and E.
Figure 1A:
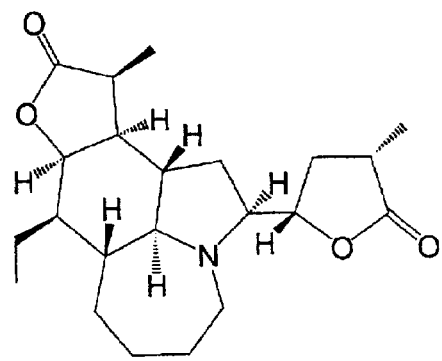
Figure 1A:
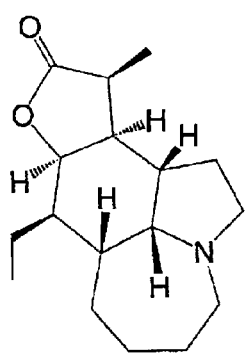
Figure 1A:
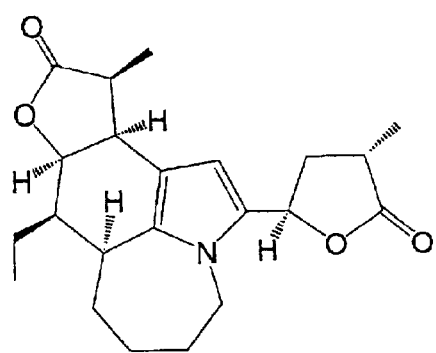
Figure 1B:
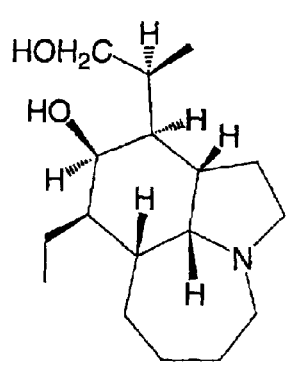
FIG. 1B shows the chemical structural formulae of three synthetic plant alkaloids, compounds F, G, and H.
Figure 1B:
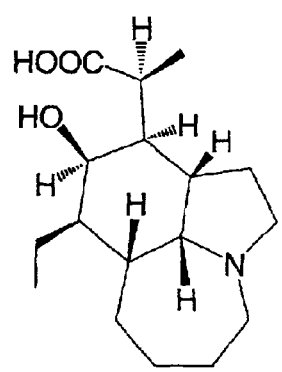
Figure 1B:
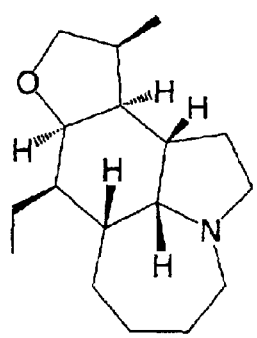
Figure 1C:
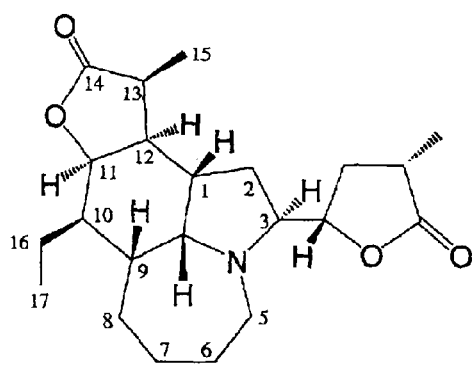
FIG. 1C shows the chemical structural formula of the isolated plant alkaloid, neotuberostemonine (compound A).

In one aspect, the antitussive compounds have Formula I:

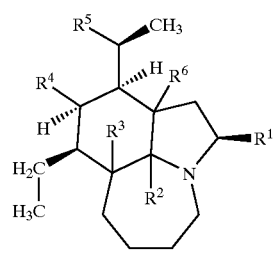

wherein $R^1$, $R^2$, $R^3$, $R^4$, $R^5$ and $R^6$ have been previously defined. FIG. 1A shows the chemical structural formulae of four isolated novel *Stemona* alkaloids, compounds B, C, D and E. FIG. 1B shows the chemical structural formulae of three synthetic novel *Stemona* related alkaloids, compounds F, G, and H. FIG. 1C shows the chemical structural formula of the isolated known alkaloid, neotuberostemonine (compound A). In particularly preferred embodiments, the alkaloids of the present invention are represented by the chemical structural formulae of compounds A, B, C, D, E, F, G, or H, as set forth in Table I.

TABLE 1

Chemical structural formulae of compounds A, B, C, D, E, F, G and H

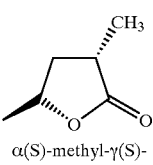

I

| Comp | R¹ | R² | R³ | R⁴ | R⁵ | R⁶ |
|---|---|---|---|---|---|---|
| A | 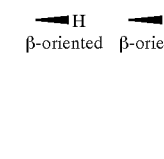<br>α(S)-methyl-γ(S)-butyroylactonyl | ◄H<br>β-oriented | ◄H<br>β-oriented | | 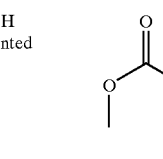 | ◄H<br>β-oriented |
| B | 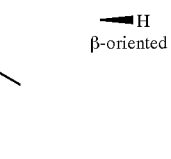<br>α(S)-methyl-γ(S)-butyroylactonyl | ⋯H<br>α-oriented | ⋯H<br>α-oriented | | 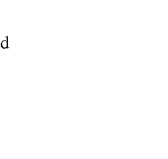 | ◄H<br>β-oriented |
| C | <br>α(S)-methyl-γ(S)-butyroylactonyl | ⋯H<br>α-oriented | ◄H<br>β-oriented | |  | ◄H<br>β-oriented |
| D | H | ◄H<br>β-oriented | ◄H<br>β-oriented | |  | ◄H<br>β-oriented |
| E | 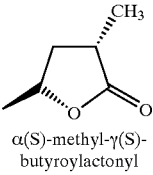 | | | | | |
| F | H | ◄H<br>β-oriented | ◄H<br>β-oriented | ◄OH | —CH₂—OH | ◄H<br>β-oriented |
| G | H | ◄H<br>β-oriented | ◄H<br>β-oriented | ◄OH | —COOH | ◄H<br>β-oriented |
| H | H | ◄H<br>β-oriented | ◄H<br>β-oriented | | 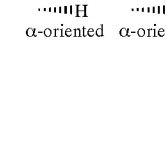 | ◄H<br>β-oriented |

The compounds of the present invention include both natural products and synthetic analogs. In certain preferred aspect, the natural products of the present invention have the following formula:

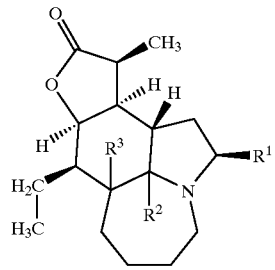

Ia wherein R$^1$ is selected from a hydrogen and an α(S)-methyl-γ(S)-butyroylactonyl; R$^2$ is selected from a β-oriented hydrogen and an α-oriented hydrogen; and R$^3$ is selected from a β-oriented hydrogen and an α-oriented hydrogen. In one preferred aspect, R$^1$ is an α(S)-methyl-γ(S)-butyroylactonyl, R$^2$ is an α-oriented hydrogen and R$^3$ is an α-oriented hydrogen, which is also referred to herein as compound B. In another preferred aspect, R$^1$ is an α(S)-methyl-γ(S)-butyroylactonyl, R$^2$ is an α-oriented hydrogen and R$^3$ is a β-oriented hydrogen, which is also referred to herein as compound C. In still another preferred aspect, R$^1$ is a hydrogen, R$^2$ is β-oriented hydrogen, and R$^3$ is β-oriented hydrogen, which is also referred to herein as compound D. In still another aspect, the compound of Formula Ia has Formula Ib, which is also referred to herein as compound E. Compound E has the formula:

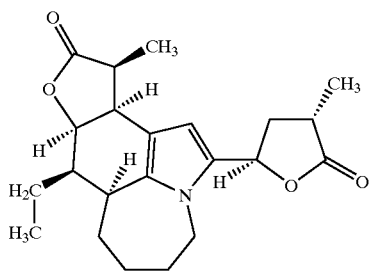

Ib

In addition to the natural products, the present invention also includes synthetic analogs. In certain preferred aspects, the natural products can be derivatized to generate compounds of Formula Ic:

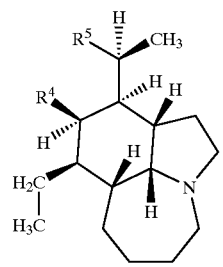

Ic wherein: R$^4$ is a hydroxyl; and R$^5$ is selected from a hydroxymethyl and a carboxyl; or alternatively, R$^4$ and R$^5$ together with the carbons to which they are attached, join to form a substituted furane ring. In one preferred aspect, R$^4$ is a hydroxyl, and R$^5$ is a hydroxymethyl, which is also referred to herein as compound F. In another preferred aspect, R$^4$ is a hydroxyl and R$^5$ is a carboxyl, which is also referred to herein as compound G. In still another preferred aspect, the compound has the formula

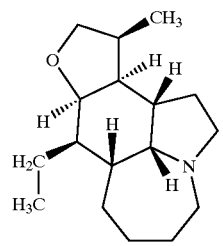

Id which is also referred to herein as compound H.

B. Methods of Making

As discussed above, the compounds of the present invention include both natural products and synthetic analogs. The naturally occurring compounds, such as compounds of Formula Ia and Ib, can be obtained from a *Stemonaceae* family plant extract, such as *S. tuberosa*. These naturally occurring compounds can be obtained from a total alkaloid extract. A total alkaloid extract can be produced using methods according to the present invention.

As such, the present invention provides a method for preparing a total alkaloid extract having antitussive activity from a *Stemonaceae* family plant, the method comprising: (a) contacting a *Stemonaceae* family plant sample with an alcohol, such as ethanol to form a liquor; (b) evaporating the alcohol in the liquor to form a syrup; (c) adjusting the syrup to an acid pH to form a supernatant fraction; (d) adjusting the supernatant fraction to a basic pH, and then extracting with an organic solvent, such as diethyl ether, to form an organic solution. The organic solution can thereafter be evaporated to dryness to form the total alkaloid extract, and can be further separated using for example, column chromatography, to obtain the pure alkaloids of interest.

In one embodiment, a silica gel column is eluted successively with a discontinuous gradient solvent system to yield fractions containing alkaloids of the present invention. The fractions can be monitored using well-known techniques to those of skill in the art. The fractions can thereafter be crystallized to yield compounds B, C, D, and E.

In certain aspect, the naturally occurring alkaloids of the present invention possess a fused lactone ring. These lactone ring functionalities can be derivatized or reduced to generate additional compounds of the present invention. In one preferred aspect, compound D is reduced with lithium aluminum hydride to yield compounds F or H. In another aspect, the lactone ring of compound D is hydrolyzed to yield compound G. As such, in certain aspects, the present invention provides methods of making compounds of Formula Ic and Id.

C. Plant Extracts

In another embodiment, the present invention provides a plant extract having antitussive activity. In some preferred embodiments, the plant extract is a *Stemonaceae* family plant extract having antitussive activity, wherein the *Stemonaceae* family plant extract inhibits a cough in a subject. In certain aspects, the genus belonging to the *Stemonaceae* family is for example, *Stemona, Croomia,* or *Stichoneuron*. Preferably, the genus is *Stemona* or *Croomia*. The species of the *Stemona* or *Croomia* genus can be for example, *S. collinsae, S. japonica, S. mairei, S. parviflora, S. sessilifolia,*

*S. tuberosa, C. japonica,* and *C. heterosepala.* (C. represents *Croomia*). Preferably, the *Stemona* species is *Stemona tuberosa.* As discussed above, the plant extract can be an aqueous extract or a total alkaloid extract. The plant extract can comprise natural products, such as compounds of Formula Ia, Ib, and compound A described in Table 1 and mixtures thereof.

In one embodiment, the present invention provides a method for preparing a total alkaloid extract having antitussive activity from a *Stemonaceae* family plant, comprising: (a) contacting a *Stemonaceae* family plant sample with an alcohol to form a liquor; (b) evaporating the alcohol in the liquor to form a syrup; (c) adjusting the syrup to an acid pH to form a supernatant fraction; (d) adjusting the supernatant fraction to a basic pH, and then extracting with an organic solvent to form an organic solution; and (e) evaporating the organic solvent to dryness to form a total alkaloid extract having antitussive activity.

In another embodiment, the present invention provides a method for preparing an aqueous extract having antitussive activity from a *Stemonaceae* family plant, comprising: (a) contacting a *Stemonaceae* family plant sample with an aqueous solvent to form a liquor; and (b) evaporating the liquor to dryness to form an aqueous extract having antitussive activity.

D. Compositions

In one embodiment, the present invention provides a pharmaceutical composition comprising the compounds of the present invention or an extract and a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for oral administration can consist of (a) liquid solutions, such as an effective amount of the alkaloid dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

In a preferred embodiment, the compositions of the present invention are used in the treatment of coughs. In a preferred embodiment the invention provides a long-lasting cough composition. The dosages of the above compositions can vary depending on many factors such as the pharmacodynamic characteristics of the particular substance, and its mode and route of administration; age, health, and weight of the individual recipient; nature and extent of symptoms, kind of concurrent treatment, frequency of treatment, and the effect desired.

The compositions of the present invention preferably contain suitable pharmaceutical carriers or diluents. Suitable pharmaceutical carriers and methods of preparing pharmaceutical dosage forms are described in *Remington's Pharmaceutical Sciences,* Mack Publishing Company, a standard reference text in this field. Suitable pharmaceutical diluents, excipients, or carriers suitable selected with respect to the intended form of administration, that is, oral tablets, capsules, elixirs, syrups and the like, consistent with conventional pharmaceutical practices. The compositions are preferably for oral delivery, more preferably in the form of a capsule or syrup, such as a cough syrup.

For oral administration in liquid form, the oral active substances can be combined with any oral, non-toxic, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like. Cough formulations generally include (in addition to the active ingredients) sorbitol, saccharose, citric acid, flavoring and water.

For oral administration in the form of a table or capsule, the active substances can be combined with an oral, non-toxic, pharmaceutically acceptable, inert carrier such as lactose, starch, sucrose, glucose, methyl, cellulose, magnesium stearate, dicalcium phosphate, calcium sulfate, mannitol, sorbitol and the like. Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavoring agents to increase subject acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propylparaben, and chlorobutanol.

The compounds of the invention may also be administered in the form of liposome delivery systems, such as small unilamellar vesicles, large unilamellar vesicles, and multilamelar vesicles. Liposomes can be formed from a variety of phospholipids, such as cholesterol, stearylamine, or phosphatidylcholines. The compounds of the invention may also be coupled with soluble polymers which are targetable drug carriers. Examples of such polymers include polyvinylpyrrolidone, pyran copolymer, polyhydroxypropyl-methacrylamide-phenol, polyhydroxyethylaspartamidephenol, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

More than one compounds of the invention may be used in a composition. The compounds can be administered concurrently, separately or sequentially.

E. Methods of Using

The present invention provides a method for suppressing cough in a mammal comprising the step of administering a pharmaceutically effective amount of an alkaloid represented by the chemical structural formulae of compound A, B, C, D, E, F, G, H or combinations and mixtures thereof. In another aspect, the present invention provides a method for reducing coughing in a subject, comprising: administering a pharmaceutically effective amount of a *Stemonaceae* family plant extract having antitussive activity, wherein the *Stemonaceae* family plant extract inhibits a cough in a subject.

The dose administered to a subject, in the context of the present invention should be sufficient to effect a beneficial therapeutic response in the subject over time. The dose will be determined by the condition of the subject. The size of the dose also will be determined by the existence, nature, and extent of any adverse side effects that accompany the administration to a particular subject. In determining the effective amount of alkaloid to be administered to achieve antitussive effect, standard dosing regimens may be used as known in the art. Karlsson et al., Pulmonary Pharmacology and Therapeutics (1999) 12:215–238.

In another aspect, the present invention features a method for preparing an isolated alkaloid for administering to an animal to reduce coughing, comprising: (a) providing a plant sample; (b) contacting the plant sample with an alcohol so that soluble plant chemical compositions are extracted from the plant sample into the alcohol to form a liquor; (c) evaporating the alcohol in the liquor to form a syrup; (d) adjusting the syrup to an acid pH and separating out particulate matter in the syrup to form a supernatant fraction; (e) adjusting the supernatant fraction to a basic pH and extracting the soluble plant chemical compositions with at least one solvent to form an organic solution; (f) evaporating the organic solution to dryness to form a total alkaloid extract; (h) purifying, separating and crystallizing the total alkaloid extract to form an isolated alkaloid; and (i) administering the isolated alkaloid to an animal having coughing episodes, thereby, reducing or suppressing the coughing episodes.

Figure 2A:
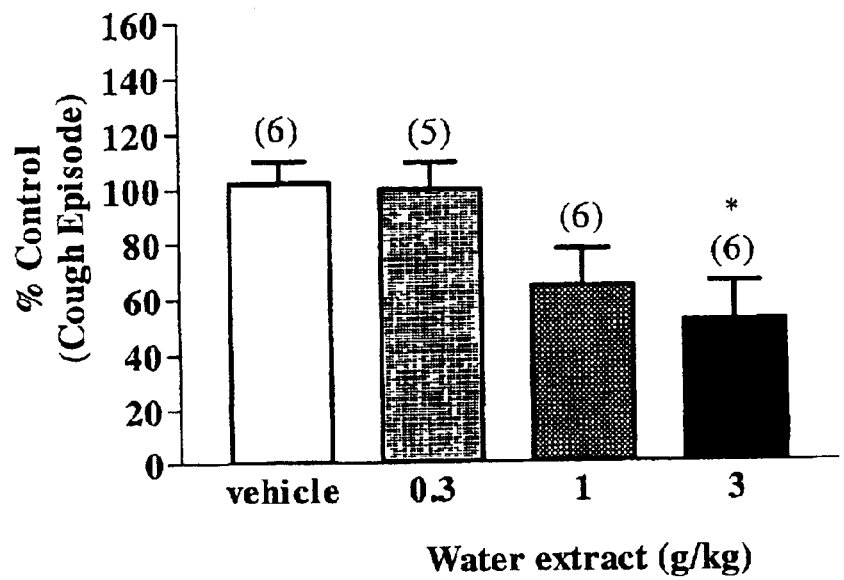
FIG. 2A shows the percentage of cough episodes of the control.
Figure 2B:
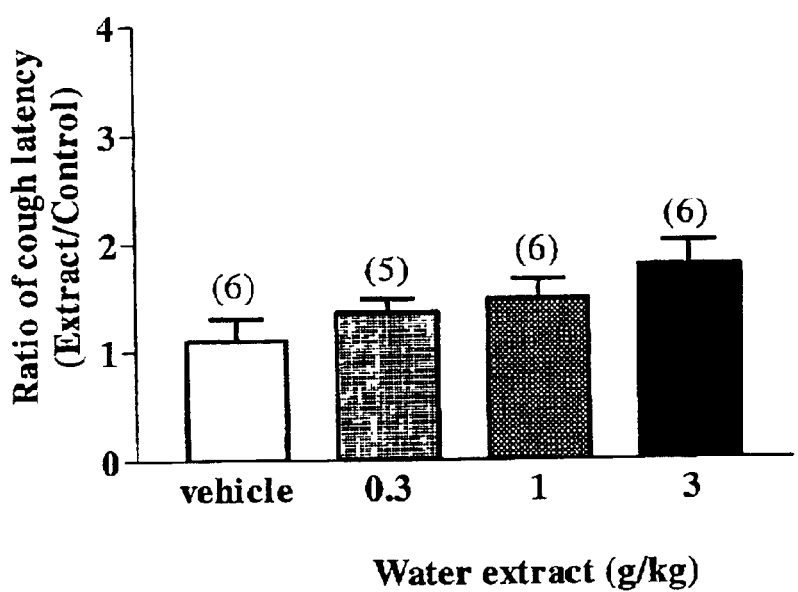
FIG. 2B shows the ratio of cough latency between the extract and the control. The number of animals tested is indicated in the parenthesis. *P<0.05 compared with the vehicle control.

As set forth in FIG. 2, an aqueous extract having antitussive activity significantly inhibited citric acid-induced cough by about 50% at a high dose of 3 g/kg and increased cough latency along with increase in dosage. FIGS. 2A-B illustrate the antitussive effects of the aqueous extract derived from *Stemona tuberosa*. FIG. 2A shows the percentage of cough episodes of the control and FIG. 2B shows the ratio of cough latency between the extract and the control.

Figure 3A:
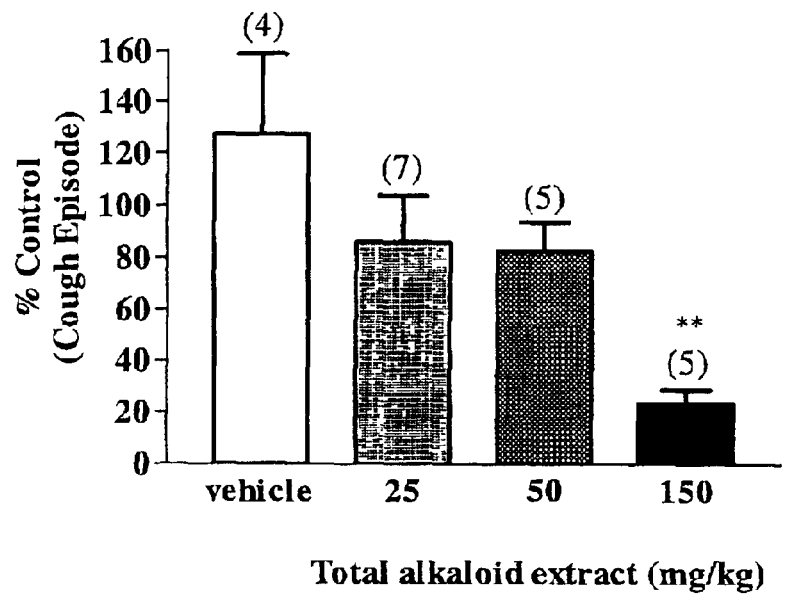
FIG. 3A shows the percentage of cough episodes of the control.
Figure 3B:
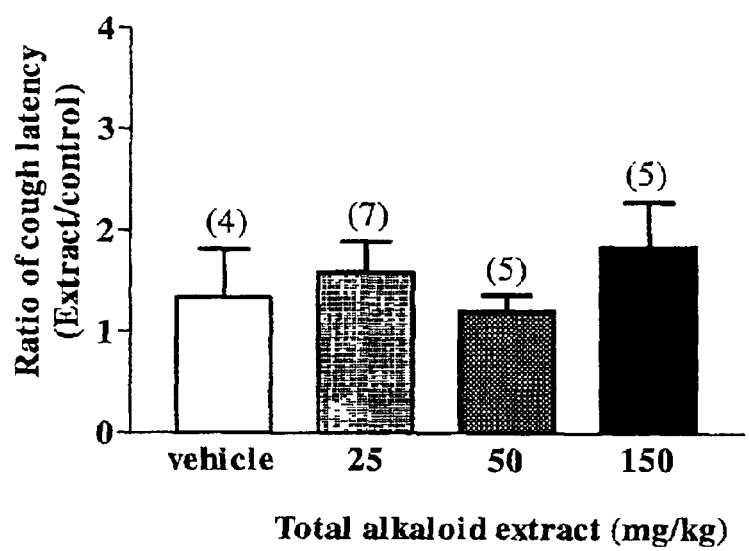
FIG. 3B shows the ratio of cough latency between the extract and the control. The number of animals tested is indicated in the parenthesis. **P<0.01 compared with the vehicle control.

At a dose of 150 mg/kg, the total alkaloid extract significantly reduced the number of coughs (see, FIG. 3). The results demonstrated that total alkaloid extract derived from *Stemona tuberosa* is effective against cough. Furthermore, the results also indicated that the antitussive activity produced by the total alkaloid extract is very potent and thus, *Stemona* alkaloids present in such extract produce the antitussive activity.

In another embodiment, a method is provided for screening for a substance that inhibits coughing activity. For example, a guinea pig is challenged with 0.5 M citric acid. Those producing more than 10 cough episodes during a first citric acid challenge are selected to be sensitive to citric acid induction and are used for further antitussive tests. The number of coughs and the cough latency in the first challenge animal are recorded as the basal level control. After 48 hours of recovery, the sensitive guinea pigs are selected and are randomly divided into different group, and then pretreated with either intraperitoneal or oral administration. For the intraperitoneal administration, the administration can be of a aqueous extract (0.3–3 g/kg), a total alkaloid extract (25–150 mg/kg), an alkaloid, for example compound A (10, 30, 50, and 100 mg/kg), or compounds B, C, D, F, G, H (133 $\mu$mol/kg), for 30 min, or of an extract suspected of having antitussive activity. For the oral administration, the administration can be of compound A or E (400 $\mu$mol/kg) for 60 min, or of an extract suspected of having antitussive activity. A second citric acid exposure is then conducted. Antitussive activity is evaluated in each treated animal as the reduction of coughs and the increase of cough latency, as compared to the basal level control.

The potency of antitussive activity produced by each alkaloid tested was compared statistically using GraphPad PRISM software (Version 3.00 for Windows 95 and NT, GraphPad Software Inc., San Diego, Calif., USA). Parametric tests were used where possible, since the preliminary study indicated that the data based on cough episode and latency pass in the normality test. To compare the potency between two groups with different treatments, a paired or unpaired T-test was performed, and the groups selected for matched or unmatched data. For comparison among different groups, a one-way analysis of variance (ANOVA) followed by a Bonfferoni's test was performed. The probability (P) value of less than 0.05 obtained from the results of the comparison of different groups was considered to be statistically significant different. Based on the statistical results of these tests, the potency of all the tested alkaloids was determined and the relationship between structure and activity was defined.

II. EXAMPLES

Materials

1. Instrumentation

Melting points were measured using a Fisher Scientific instrument and were uncorrected. Optical rotations were recorded on a Perkin-Elmer 341 Polarimeter in MeOH solution. IR spectra were recorded on a Nicolet Impact 420 FT-IR spectrometer. EI-MS was performed on a Finnegan MAT GCQ with a direct loop injection, while ESI-MS was recorded on a Finnegan MAT TSQ 7000 instrument. NMR spectra ($^1$H and $^{13}$C NMR) were recorded on either a 500 MHz or 300 MHz Bruker spectrometer in $CDCl_3$. The chemical shifts are reported in $\delta$ (ppm) with TMS as an internal standard and coupling constants (J) are given in Hz. X-ray diffractions for compounds B, C and D were conducted on a Bruker SMART CCD diffractometer and those for compounds A, E and F were conducted on a Bruker P4 diffractometer. Merck silica gel (60 $F_{254}$) precoated on an aluminum sheet was used for thin layer chromatography (TLC), on which the spots were detected by spraying with Dragendorff reagent. Merck silica gel (70–230 mesh) was used for column chromatography.

2. Plant Material

The dried root tuber of *Stemona tuberosa* used in the above experiments was purchased from a Chinese herbal store in Hong Kong, and verified as *Stemona tuberosa*. A voucher specimen (#992300) of this plant material has been deposited in the museum of Institute of Chinese Medicine, The Chinese University of Hong Kong, Hong Kong.

3. Animals

Male adult Dunkin-Hartley guinea pigs (body weight 300–500 g), supplied by the Laboratory Animal Services Center, the Chinese University of Hong Kong, were used in this invention. The guinea pigs were maintained in climatized colony-rooms (temperature 21±1° C.; humidity 60%) on a natural light/dark cycle with access to standard food and water.

Example 1

Production of Aqueous Extract

Dried root tubers of *Stemona tuberosa* (10 g) were chopped into small pieces and extracted with distilled water under reflux for 2 hr. After filtration the water solution was evaporated to dryness to yield a aqueous extract (3.5 g).

Example 2

Production of Total Alkaloid Extract

To obtain a total alkaloid extract, 6 kg of dried root tubers of *Stemona tuberosa* was chopped into small pieces and refluxed with 95% ethanol for 2 hr. The warm extract liquor was poured out and allowed to stand overnight at 10° C. Thereafter, the liquor was filtered, and the filtrate evaporated under reduced pressure to obtain a syrup. The syrup was acidified with diluted hydrochloride solution (4%) and centrifuged at 3000 RPM, 5° C., for 40 min. The supernatant was basified with aqueous ammonium hydroxide to pH 9 and sequentially extracted with diethyl ether and chloroform, respectively. The combined organic solution was then evaporated to dryness resulting in a total alkaloid extract (24 g).

Example 3

Isolation of Five Stemona Alkaloids (Compounds A–E)

The total alkaloid extract (24 g) of Example 2 was dissolved in diethyl ether with refluxing, then left overnight at room temperature, to give a light yellow precipitate, the crude compound A (3.4 g). The crude compound A was further crystallized with ethanol resulting in a pure alkaloid (Compound A, 2.5 g). The combined mother liquor was evaporated to dryness, to form a mixture of alkaloids. The mixture of alkaloids was then subjected to silica gel column chromatography, and eluted successively with a discontinuous gradient solvent of $CHCl_3$:MeOH:$NH_4OH$ (98:2:0.05), (96:4:0.05) and (92:8:0.05), respectively. The eluant was monitored by Thin Layer Chromatography (TLC) and pooled into four fractions 1–4. Fraction 1 (0.9 g) eluted with $CHCl_3$:MeOH:$NH_4OH$ (98:2:0.05) was further purified by silica gel column chromatography with hexane-EtOAc (70:30) elution to yield compound E (Eipbisdehydrotuberostemonine J, 380 mg). Fraction 2 (0.8 g) eluted with $CHCl_3$:MeOH:$NH_4OH$ (98:2:0.05) was further purified by silica gel column chromatography with hexane-EtOAc (60:40) elution, resulting in Compound B (Tuberostemonine J, 245 mg). Fraction 3 (2.3 g) eluted with $CHCl_3$:MeOH:$NH_4OH$ (96:4:0.05) was further fractionated by silica gel column chromatography with hexane-EtOAc (50:50) elution, resulting in Compound C (Tuberostemonine H, 470 mg) and Compound A (98 mg), respectively. Fraction 4 (3.1 g) eluted with $CHCl_3$:MeOH:$NH_4OH$ (92:8:0.05) was fractionated by silica gel column chromatography with hexane-EtOAc (35:65) elution to obtain Compound D (Neostenine, 600 mg).

The characteristics of each compound are given below.

Figure 8:
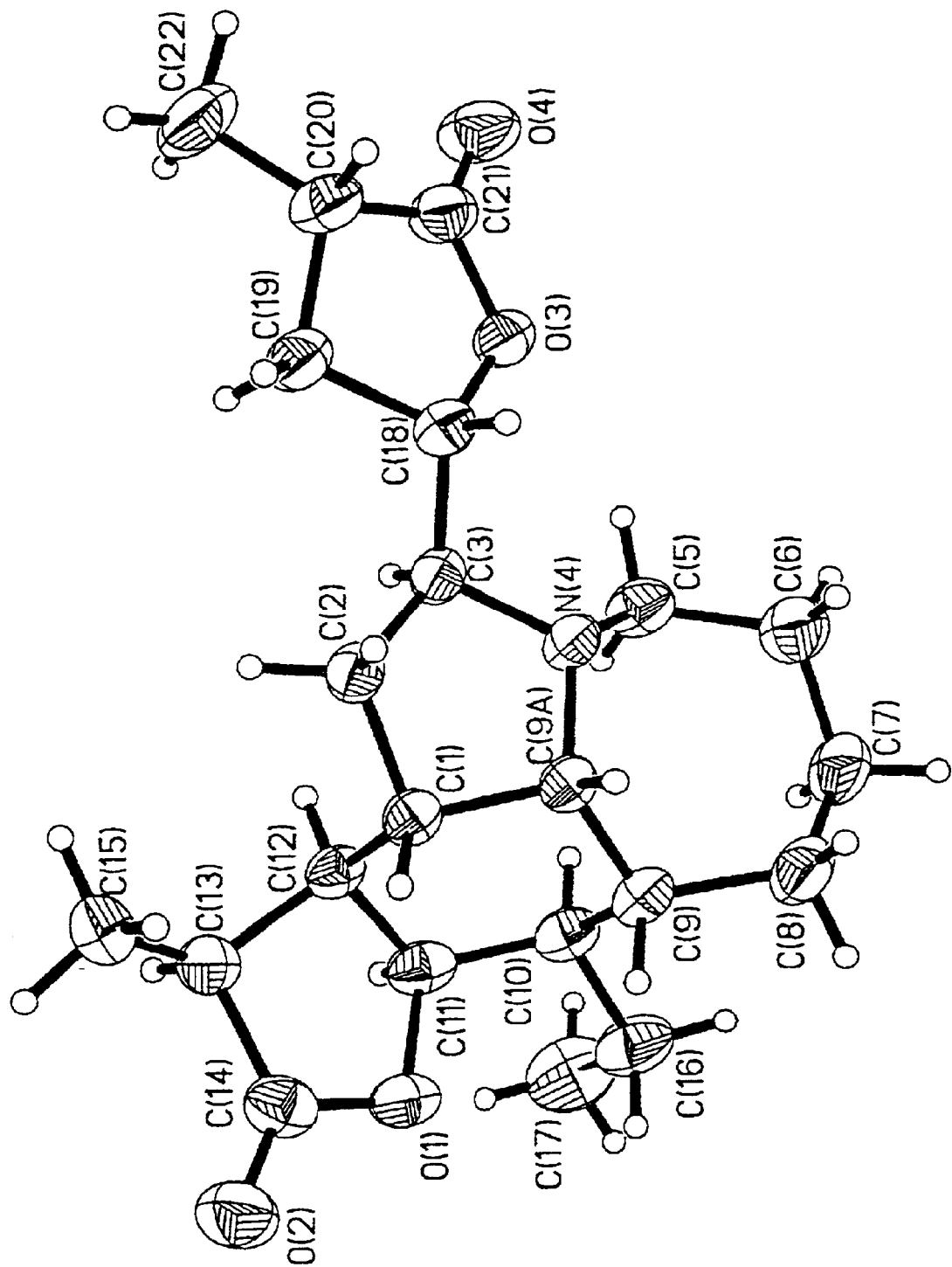
FIG. 8 shows the molecular structure of compound A.

Compound A (Neotuberostemonine): A colorless needle crystallized from hexane/EtOAc. mp: 159.5–161° C.; $[\alpha]_D^{20}$=+83° (c, 0.1; MeOH); IR $\nu_{max}^{KBr}$ $cm^{-1}$: 1762, 1456, 1167, 1015; ESI-MS m/z (% intensity): 376 $[M+H]^+$ (63); EI-MS m/z (% intensity): 375 $[M]^+$ (5), 276 $[M-C_5H_7O_2]^+$ (100). $^1$H NMR (300 MHz, $CDCl_3$) δ: 0.96 (3H, t, J=7.3 Hz, H-17), 1.20 (3H, d, J=7.1 Hz, H-15), 1.22 (3H, d, J=7.0 Hz, H-22), 1.3–2.0 (14H, H-1, 2H-2, 2H-6, 2H-7, 2H-8, H-9, H-10, 2H-16, H-19), 2.05 (1H, ddd, J=15.0, 3.3, 6.6 Hz, H-12), 2.34 (1H, ddd, J=5.4, 13.3, 15.2 Hz, H-19), 2.58 (1H, ddq, J=5.3, 7.0, 12.1 Hz, H-20), 2.84 (1H, dq, J=6.6, 6.9 Hz, H-13), 2.92 and 3.03 (each 1H, m, 2H-5), 3.16 (1H, dd, J=3.8, 3.9 Hz, H-9a), 3.29 (1H, dd, J=7.7, 14.0 Hz, H-3), 4.36 (1H, ddd, J=5.4, 7.7, 11.2 Hz, H-18), 4.49 (1H, dd, J=3.3, 3.0 Hz, H-11). The X-ray diffraction data are summarized in Table 2 and FIG. 8.

Figure 9:
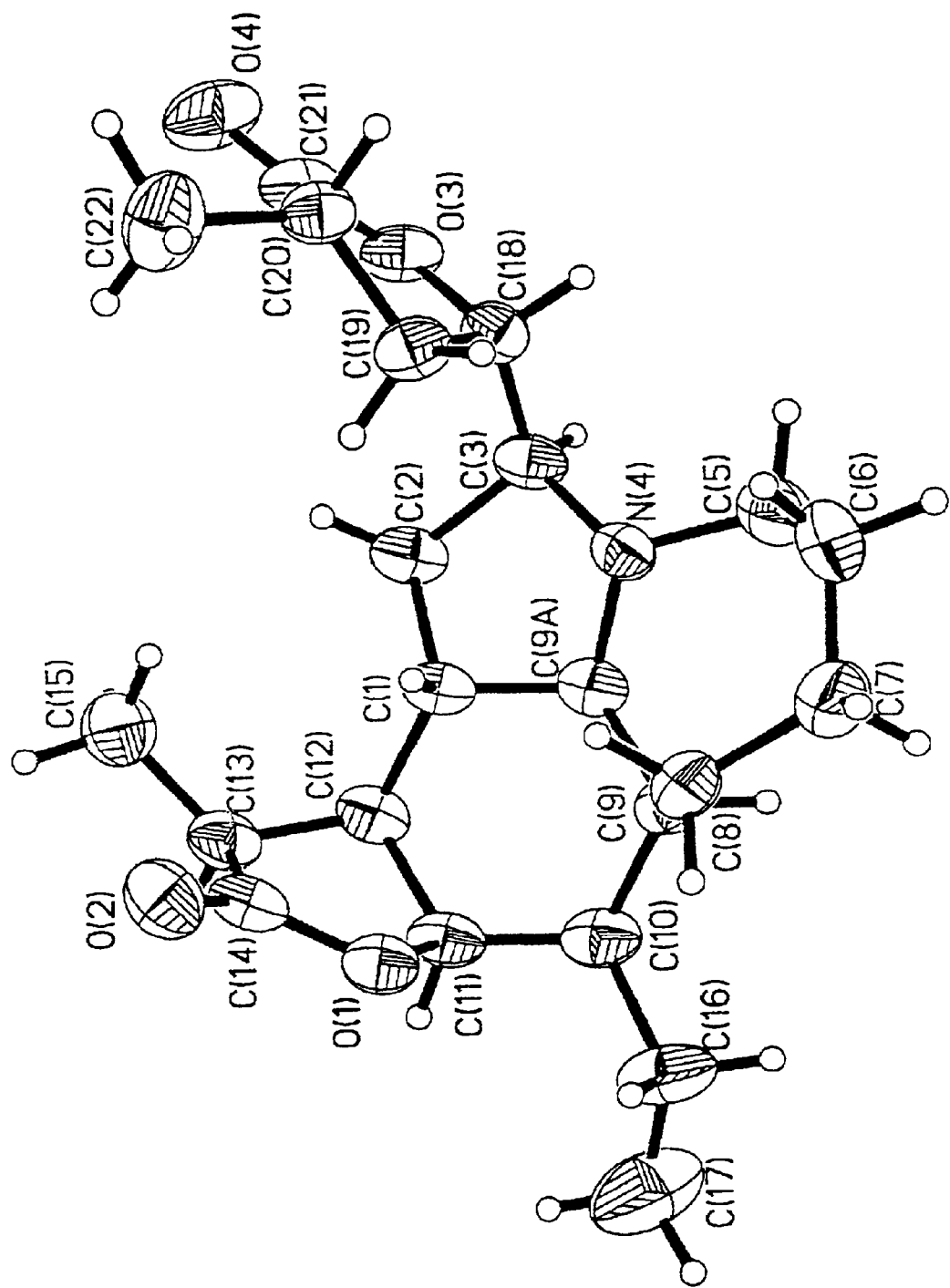
FIG. 9 shows the molecular structure of compound B.

Compound B (Tuberostemonine J): A colorless prism crystallized from hexane/EtOAc. mp: 180–182° C.; $[\alpha]_D^{20}$=+36.4° (c, 0.1; MeOH); EI-MS m/z (% intensity): 375 $[M]^+$ (1.5), 276 $[M-C_5H_7O_2]^+$ (100). $^1$H NMR (500 MHz, $CDCl_3$) δ: 1.01(3H, t, J=7.5 Hz, H-17), 1.18 (3H, d, J=7.5 Hz, H-15), 1.22 (3H, d, J=7.5 Hz, H-22), 1.40–2.10 (15H, H-1, 2H-2, 2H-6, 2H-7, 2H-8, H-9, H-10, H-12, 2H-16, H-19), 2.25 (1H, m, H-19), 2.50 (1H, m, H-20), 2.74 (1H, m, H-13), 2.74 and 2.98 (each 1H, m, 2H-5), 3.02 (2H, m, H-3 and H-9a), 4.19 (1H, br, H-11), 4.37 (1H, m, H-18); $^{13}$C NMR (125 MHz, $CDCl_3$) δ: 11.60 (C-17), 12.90 (C-15), 14.80 (C-22), 25.45 (C-16), 29.45 (C-7), 30.62 (C-6), 32.40 (C-2), 33.27 (C-8), 34.30 (C-19), 34.52 (C-9), 34.77 (C-10), 38.38 (C-12), 41.11 (C-20), 45.05 (C-13), 45.80 (C-1), 50.09 (C-5), 64.59 (C-3), 66.28 (C-9a), 80.18 (C-11), 81.28 (C-18), 179.18 (C-14), 179.26 (C-21). The X-ray diffraction data are summarized in Table 2 and FIG. 9.

Figure 10:
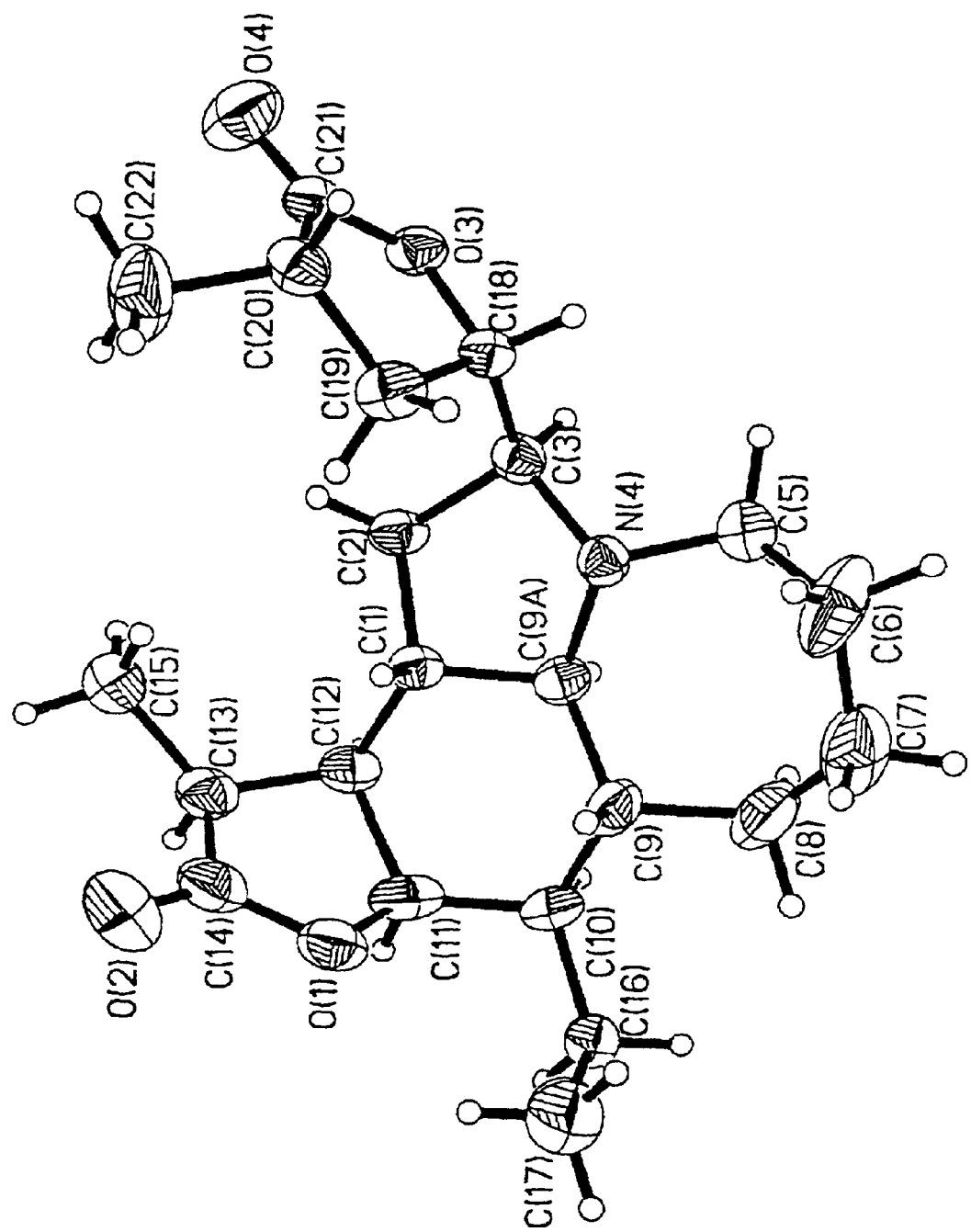
FIG. 10 shows the molecular structure of compound C.

Compound C (Tuberostemonine H): A colorless needle crystallized from hexane/EtOAc. mp: 183–185° C.; $[\alpha]_D^{20}$=+77.6°(c, 0.1; MeOH); IR $\nu_{max}^{KBr}$ $cm^{-1}$: 1769, 1454, 1174, 1016; EI-MS m/z (% intensity): 375 $[M]^+$ (0.9), 276 $[M-C_5H_7O_2]^+$ (100). $^1$H NMR (500 MHz, $CDCl_3$) δ: 1.00 (3H, t, J=7.2 Hz, H-17), 1.18 (3H, d, J=7.2 Hz, H-15), 1.22 (3H, d, J=7.2 Hz, H-22), 1.3–2.0 (15H, H-1, 2H-2, 2H-6, 2H-7, 2H-8, H-9, H-10, H-12, 2H-16, H-19), 2.35 (1H, m, H-19), 2.45 (1H, m, H-20), 2.61 (1H, m, H-13), 2.78 and 2.84 (each 1H, m, 2H-5), 3.01 (1H, m, H-9a), 3.20 (1H, m, H-3), 4.37 (1H, ddd, J=4.6, 5.9, 10.5 Hz, H-18), 4.57 (1H, d, J=3.6 Hz, H-11); $^{13}$C NMR (125 MHz, $CDCl_3$) δ: 11.61 (C-15), 11.88 (C-17), 15.05 (C-22), 21.17 (C-16), 24.10 (C-7), 27.10 (C-8), 27.34 (C-6), 31.15 (C-2), 33.42 (C-19), 35.31 (C-10), 41.10 (C-9), 41.90 (C-20), 44.14 (C-12), 44.84 (C-1), 47.22 (C-13), 54.70 (C-5), 67.46 (C-9a), 77.97 (C-3), 79.24 (C-18), 80.67 (C-11), 179.10 (C-21), 179.45 (C-14). The X-ray diffraction data are summarized in Table 2 and FIG. 10.

Figure 11:
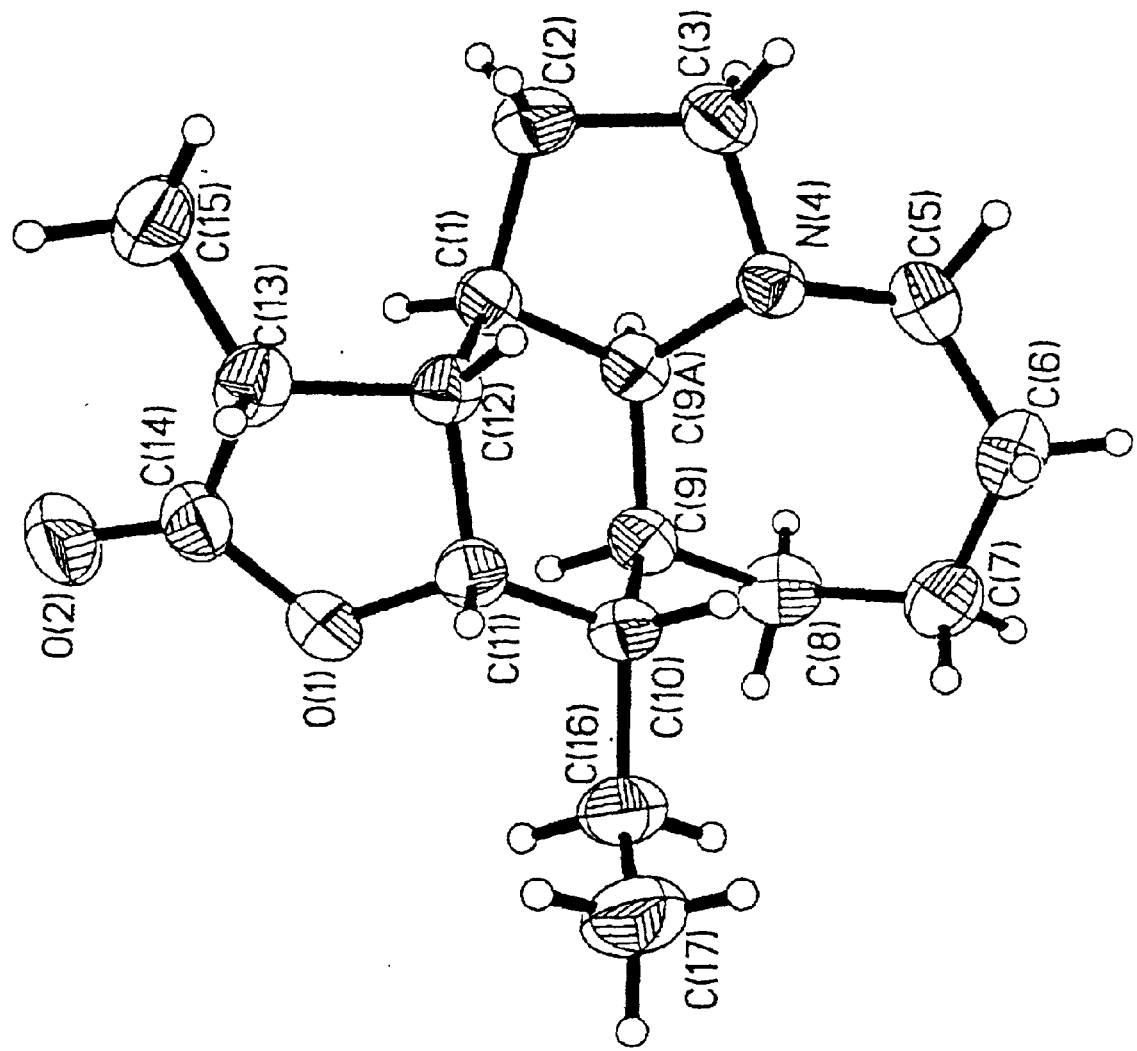
FIG. 11 shows the molecular structure of compound D.

Compound D (Neostenine): A colorless prism crystallized from hexane/EtOAc. mp: 90–92° C.; $[\alpha]_D^{20}$=+73.6° (c, 0.1; MeOH); EI-MS m/z (% intensity): 277 $[M]^+$ (74), 276 $[M-H]^+$ (100), 233 (32), 204 (76), 191(67). $^1$H NMR (500 MHz, $CDCl_3$) δ: 0.97 (3H, t, J=7.5 Hz, H-17), 1.20 (3H, d, J=7.2 Hz, H-15), 1.3–2.0 (14H, H-1, 2H-2, 2H-6, 2H-7, 2H-8, H-9, H-10, H-12, and 2H-16), 2.27 (1H, m, H-13), 2.45 (2H, m, H-3), 2.81 and 2.89 (each 1H, m, 2H-5), 3.22 (1H, m, H-9a), 4.50 (1H, br, H-11); $^{13}$C NMR (125 MHz, $CDCl_3$) δ: 10.67 (q, C-17), 11.84 (q, C-15), 21.63 (t, C-16), 21.70 (t, C-7), 28.67 (t, C-8), 28.86 (t, C-6), 30.65 (t, C-2), 34.79 (t, C-9), 37.81 (d, C-10), 37.97 (d, C-12), 43.04 (d, C-13), 43.38 (d, C-1), 56.28 (t, C-5), 56.44 (t, C-3), 71.52 (d, C-9a), 79.87 (d, C-11), 180.24 (s, C-14). The X-ray diffraction data are summarized in Table 2 and FIG. 11.

Figure 12:
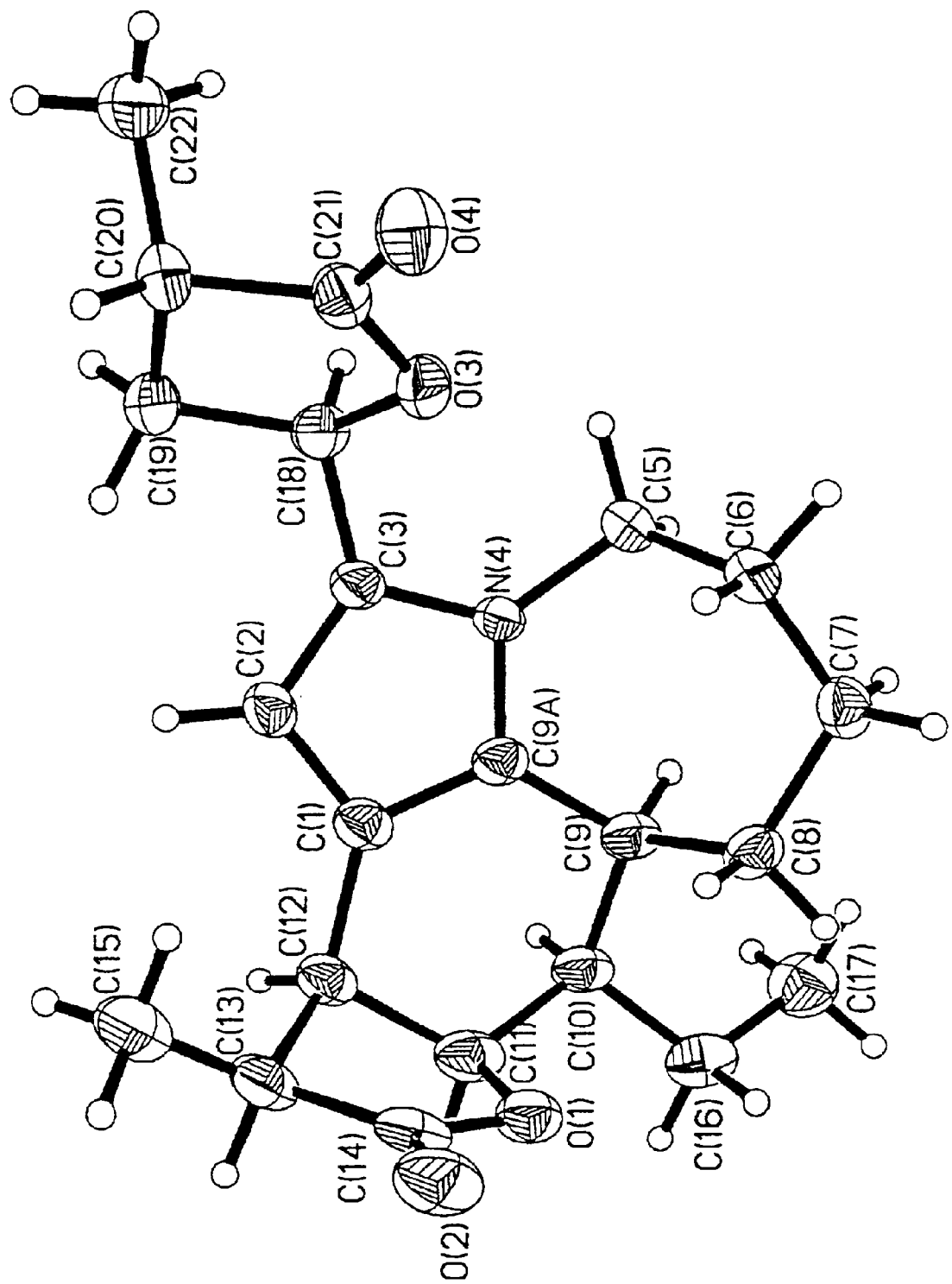
FIG. 12 shows the molecular structure of compound E

Compound E (Epibisdehydrotuberostemonine J): A colorless prism crystallized from hexane/EtOAc. mp: 186–188° C.; $[C]_D^{20}$=–16.1° (c, 0.1; MeOH); IR $v_{max}^{KBr}$ cm$^{-1}$: 2932, 2864, 1763, 1454, 1158, 997, 923; EI-MS m/z (% intensity): 371 [M]$^+$ (68), 327 (28), 298 (100), 272 [M-C$_5$H$_7$O$_2$]$^+$ (71). $^1$H NMR (500 MHz, CDCl$_3$) δ: 1.06 (3H, t, J=7.0 Hz, H-17), 1.35 (3H, d, J=7.0 Hz, H-22), 1.37 (3H, d, J=7.0 Hz, H-15), 1.47 (1H, t, J=11.5 Hz, H-10), 1.80 (2H, m, H-16), 1.95 (2H, m, H-8), 2.06 and 1.16 (each 1H, m, 2H-6), 2.08 and 1.47 (each 1H, m, 2H-7), 2.07 (1H, d, J=11 Hz, H-19), 2.7–2.9 (3H, m, H-13, H-19, H-20), 3.01 (1H, t, J=7.0 Hz, H-9), 3.56 (1H, dd, J=5.0, 5.8 Hz, H-12), 3.79 (1H, dd, J=13.3, 14.0 Hz, H-5), 4.24 (1H, dd, J=5.0, 14.0 Hz, H-5), 4.67 (1H, d, J=4.0 Hz, H-11), 5.36 (1H, dd, J=5.0, 11.0 Hz, H-18), 5.99 (1H, s, H-2); $^{13}$C NMR (125 MHz, CDCl$_3$) δ: 11.39 (C-17), 11.88 (C-15), 14.97 (C-22), 23.25 (C-16), 28.58 (C-6), 28.88 (C-7), 30.97 (C-19), 34.87 (C-10), 35.04 (C-8), 36.10 (C-9), 39.57 (C-12), 41.80 (C-13), 41.94 (C-20), 44.85 (C-5), 71.70 (C-18), 80.89 (C-11), 107.13 (C-2), 108.59 (C-1), 126.60 (C-9a), 137.58 (C-3), 178.87 (C-14), 178.87 (C-21). The X-ray diffraction data are summarized in Table 2 and FIG. 12.

Example 4

Synthesis of Analogs of Compound D: Compounds F, G. and H 4.1 Synthesis of Compound F A mixture of Compound D (250 mg) and lithium aluminum hydride (120 mg) was heated under reflux in tetrahydrofuran with stirring for 3 hrs. After cooling, a few drops of water was added to the mixture to destroy the excess lithium aluminum hydride. The mixture was filtered and the filtrate was evaporated to dryness under reduced pressure at 40° C. to obtain a white residue. The residue was dissolved in a 4% hydrochloride solution and then extracted with diethyl ether to remove non-alkaloid compounds. The aqueous layer was separated out and basified with 25% ammonium hydroxide, and then extracted with diethyl ether. The diethyl ether layer was washed with water and evaporated to yield dried powders, which were crystallized from hexane-EtOAc to give prisms (165 mg). The resulting synthetic compound was named Neostenine-diol. The characteristics of Neostenine-diol are as follows.

Fine prismatic crystals from hexane-EtOAc; mp 130–132° C.; ESI-MS m/z (% intensity): 282 [M+H]$^+$ (100). $^1$H NMR (300 MHz, CDCl$_3$) δ: 0.93 (3H, t, J=7.5 Hz, H-17), 1.04 (3H, d, J=7.5 Hz, H-15), 2.4–2.7 (2H, m, H-3), 2.9–3.1 (2H, m, H-5), 3.34 (1H, m, H-9a), 3.61 (2H, m, H-14), 3.90 (1H, m, H-11); $^{13}$C NMR (75.5 MHz, CDCl$_3$) δ: 12.18 (C-17), 18.90 (C-15), 21.58 (C-7), 22.26 (C-16), 28.09

TABLE 2

Crystallographic data, parameters, and refinements of compounds A, B, C, D, E and F

| Parameter Alkaloid | Compound | | | | | |
|---|---|---|---|---|---|---|
| | A | B | C | D | E | F |
| Size (mm) | 0.30 × 0.40 × 0.75 | 0.38 × 0.36 × 0.77 | 0.22 × 0.34 × 0.65 | 0.26 × 0.28 × 0.82 | 0.12 × 0.40 × 0.72 | 0.38 × 0.30 × 0.8 |
| Chemical formula | C$_{22}$H$_{33}$NO$_4$ | C$_{22}$H$_{33}$NO$_4$ | C$_{22}$H$_{33}$NO$_4$ | C$_{17}$H$_{27}$NO$_2$ | C$_{22}$H$_{29}$NO$_4$ | C$_{17}$H$_{31}$NO$_2$ |
| Formula weight | 375.49 | 375.49 | 375.49 | 277.40 | 371.46 | 281.43 |
| Crystal system | Orthorhombic | Orthorhombic | Orthorhombic | Orthorhombic | Monoclinic | Orthorhombic |
| Space group | P2(1)2(1)2(1) | P2(1)2(1)2(1) | P2(1)2(1)2(1) | P2(1)2(1)2(1) | P2(1) | P2(1)2(1)2(1) |
| Unit cell dimension | a = 6.459(2) | a = 9.0115(11) | a = 5.5337(5) | a = 5.8368(4) | a = 6.3596(19) | a = 7.9979(14) |
| | b =14.228(3) | b =10.612(4) | b = 19.0275(18) | b = 9.6805(7) | b = 18.495(3) | b = 18.495(3) |
| | c = 23.033(3) | c = 22.074(3) | c = 20.0554(19) | c = 27.789(2) | c = 8.3875(15) β = 92.521(18) | c = 21.515(4) |
| Volume, Å$^3$ | 2116.8(9) | 2110.9 | 2111.7 | 1570.1(2) | 985.6(4) | 1640.7(5) |
| Z | 4 | 4 | 4 | 4 | 2 | 4 |
| Density (calculated) mg/m$^3$ | 1.178 | 1.182 | 1.162 | 1.173 | 1.252 | 1.139 |
| Reflections measured | 2891 | 3109 | 12774 | 7580 | 2449 | 9269 |
| Independent | 2690 | 2902 | 4138 | 2277 | 1914 | 2909 |
| Observed reflections | 1661 | 1750 | 1805 | 1744 | 1383 | 1872 |
| Parameters | 246 | 246 | 244 | 182 | 246 | 183 |
| Goodness of fit on F$^2$ | 1.060 | 1.017 | 0.999 | 0.986 | 1.048 | 0.999 |
| Final R indices [I > 4σ] | 0.050 | 0.058 | 0.069 | 0.038 | 0.045 | 0.046 |
| R indices (all data) | 0.098 | 0.108 | 0.181 | 0.058 | 0.077 | 0.092 |

Figure 13:
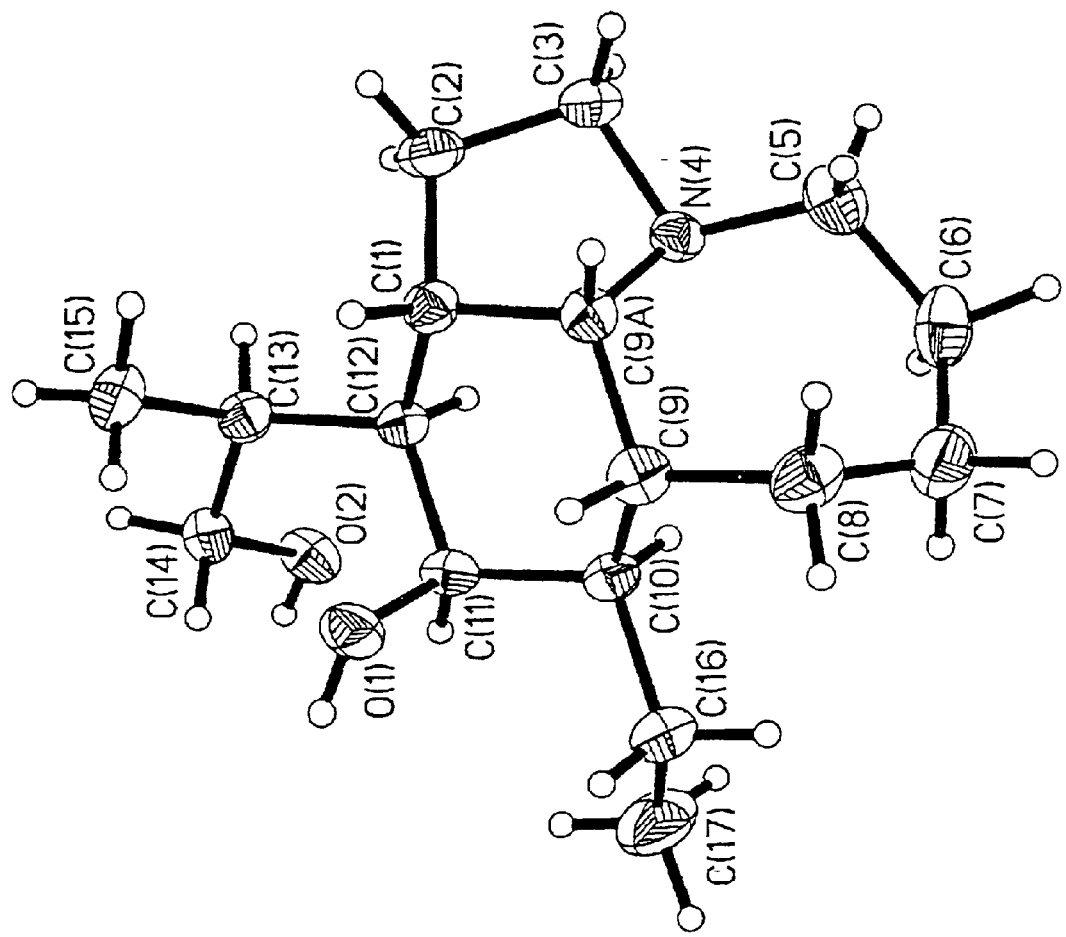
FIG. 13 shows the molecular structure of compound F.

(C-2), 29.59 (C-8), 30.03 (C-6), 35.59 (C-10), 38.58 (C-12), 39.45 (C-9), 43.83 (C-1), 44.99 (C-13), 56.87 (C-3), 58.91 (C-5), 65.49 (C-14), 71.43 (C-9a), 73.04 (C-11). The X-ray diffraction data are summarized in Table 2 and FIG. 13.

4.2 Synthesis of Compound G

Compound D (148 mg) was dissolved in 2 ml of 4% sodium hydroxide solution and heated with stirring on water both at 60° C. for 1.5 hrs. The suspended mixture changed into a clear solution. The solution was then surrounded by an ice bath, and adjusted gradually with 2% hydrochloride solution to pH 8, while stirring. Cooled distilled water was added into the resulting solution to make the final volume of 20 ml with a final concentration of 26.67 mM of the product, compound F. The resulting solution was stored at 0–5° C. This compound was named Neostenine-acid.

The ESI-MS spectrum of compound G showed only one compound with a molecular weight of 296 $[M+H]^+$ (100).

4.3 Synthesis of Compound H

A mixture of compound D (500 mg) and lithium aluminum hydride (250 mg) was refluxed with tetrahydrofuran for 4 hr. After cooling the mixture, a few drops of $H_2O$ were added to destroy the excess lithium aluminum hydride. The mixture was then filtered and the filtrate evaporated to dryness, forming a residue. The residue was dissolved in a 4% hydrogen chloride solution and then extracted with diethyl ether to remove non-alkaloid compounds. The aqueous layer was separated out and basified with 25% $NH_4OH$, and then extracted with diethyl ether. The diethyl ether solution was evaporated to dryness. The residue was heated with 20 ml of 10% $H_2SO_4$ in a water bath for 5 hr, and the acidic solution was extracted with diethyl ether, and then basified with $K_2CO_3$. The resulting basic solution was extracted with diethyl ether. The organic layer was washed with water, dried with $K_2CO_3$, and evaporated to dryness, resulting in an oil. The oil was further purified by silica gel column chromatography and eluted with a mixture of $CHCl_3$:EtOAc:MeOH (7:1:2) to obtain a colorless oil that was named Neostenine-ether (245 mg). The characteristics of this compound are as follows.

ESI-MS m/z (% intensity): 264 $[M+H]^+$ (100). $^1H$ NMR (300 $CDCl_3$) δ: 0.93 (3H, t, J=7.5 Hz, H-17), 0.98 (3H, d, J=7.5, H-15), 3.22 (1H, m, H-9a), 3.45 (1H, dd, J=8.1, 10.2 Hz, H-14), 3.87 (1H, dd, J=8.1, 8.1 Hz, H-14), 4.1 (1H, m, H-11); $^{13}C$ NMR (75.5 MHz, $CDCl_3$) δ: 12.13 (C-17), 12.97 (C-15), 21.93 (C-16), 22.19 (C-7), 29.31 (C-2), 29.49 (C-8), 31.31 (C-6), 35.09 (C-10), 37.03 (C-12), 38.69 (C-9), 38.81 (C-13), 42.89 (C-1), 56.93 (C-3), 57.13 (C-5), 72.41 (C-14), 72.64 (C-9a), 80.06 (C-11).

Example 5

Measurement of Antitussive Activity

The method previously described by Gallico et al. (1994) was adopted with the following modifications. Unrestrained guinea pigs were placed individually in a hermetically sealed transparent Perspex chamber (25 cm×12 cm×12 cm), and exposed to a nebulized aqueous solution of 0.5 M citric acid for 8 min. An ultrasonic nebulizer was used (OMRON NE-U12, Tokyo, Japan) that produced an aerosol with particles having a mass median diameter of 1~5 μm. Approximately 0.5 ml of 0.5 M citric acid solution was nebulized per minute. During the exposure, the guinea pigs were continuously monitored by a trained observer. The episodes and latency of coughing in 8 min were detected and counted by the observer. Cough sounds were recorded concurrently and amplified via a microphone placed in the chamber. The sound waves were analyzed by a personal computer by using Cool Edit 2000 software (Syntrillium, Phenix, USA). Therefore, cough counting was performed based on both acoustic data and human observations, and in this manner the reduction or inhibition of coughing (i.e., antitussive activity) was measured.

Example 6

Evaluation of Antitussive Activity of Extracts and Pure Stemona Alkaloids

The guinea pigs were first challenged with 0.5 M citric acid. Those producing more than 10 cough episodes during the first citric acid challenge were selected to be sensitive to citric acid induction and were used for the further antitussive tests. The number of coughs and the cough latency in the first challenge were recorded as the basal level control. After 48 hours of recovery, the sensitive guinea pigs were selected and were randomly divided into different groups with at least four guinea pigs in each group, and then pretreated with intraperitoneal administration of the aqueous extract (0.3–3 g/kg), the total alkaloid extract (25–150 mg/kg), compound A (10, 30, 50, and 100 mg/kg), and compounds B, C, D, F, G, H (133 μmol/kg), for 30 min before the second citric acid exposure. Antitussive activity was evaluated in each treated animal as the reduction of coughs and the increase of cough latency, as compared to the basal level control. Furthermore, the same antitussive test was also performed with oral administration of compounds A and E (400 μmol/kg). In addition, as a positive control, the antitussive activity of codeine (5, 10 and 30 mg/kg, i.p.) was also determined in a parallel study.

Example 7

Antitussive Activities of Extracts and Compound A

As set forth in FIG. 2, an aqueous extract having antitussive activity significantly inhibited citric acid-induced cough by about 50% at a high dose of 3 g/kg and increased cough latency along with increase in dosage. FIGS. 2A–B illustrate the antitussive effects of the aqueous extract derived from *Stemona tuberosa*. FIG. 2A shows the percentage of cough episodes of the control and FIG. 2B shows the ratio of cough latency between the extract and the control.

At a dose of 150 mg/kg, the total alkaloid extract significantly reduced the number of coughs (see, FIG. 3). The results demonstrated that total alkaloid extract derived from *Stemona tuberosa* is effective against cough. Furthermore, the results also indicated that the antitussive activity produced by the total alkaloid extract is very potent and thus, *Stemona* alkaloids present in such extract produce the antitussive activity.

Figure 4A:
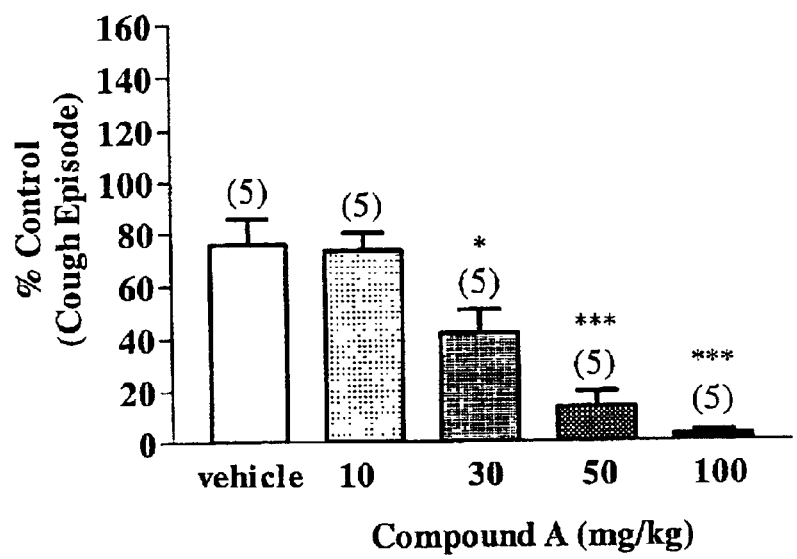
FIG. 4A shows the percentage cough episode of the control.
Figure 4B:
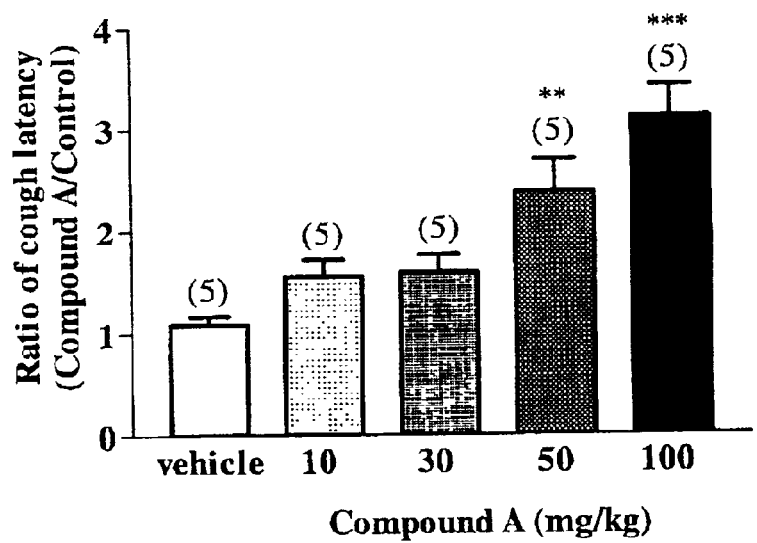
FIG. 4B shows the ratio of cough latency between compound A and the control. The number of animals tested is indicated in the parenthesis. *P<0.05, P<0.01, and *P<0.001 compared with the vehicle control.

The antitussive activity of the pure *Stemona* alkaloids isolated from *Stemona tuberosa*, compound A, inhibited citric acid-induced cough in a dose-dependent manner and also significantly increased the cough latency at the doses of 50 and 100 mg/kg (see, FIG. 4). Furthermore, a comparative study was conducted using codeine, the commonly used antitussive drug, as the positive control. The results showed that $ED_{50}$ value for compound A and codeine were comparable.

Example 8

Structure-Antitussive Activity Relationship

Figure 5A:
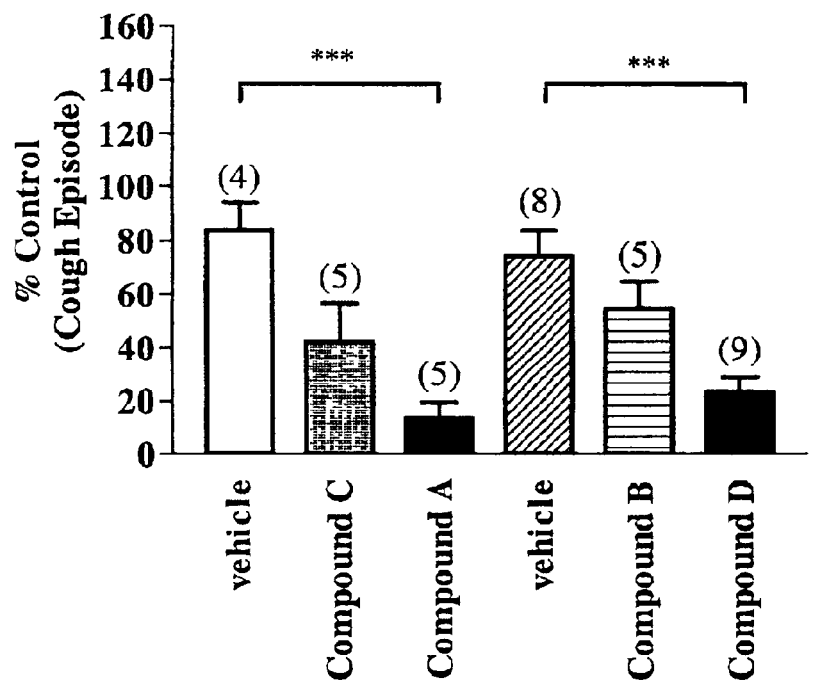
FIG. 5A shows the effects of compounds A, B, C, and D administered intraperitoneally (133 μmol/kg)
Figure 5B:
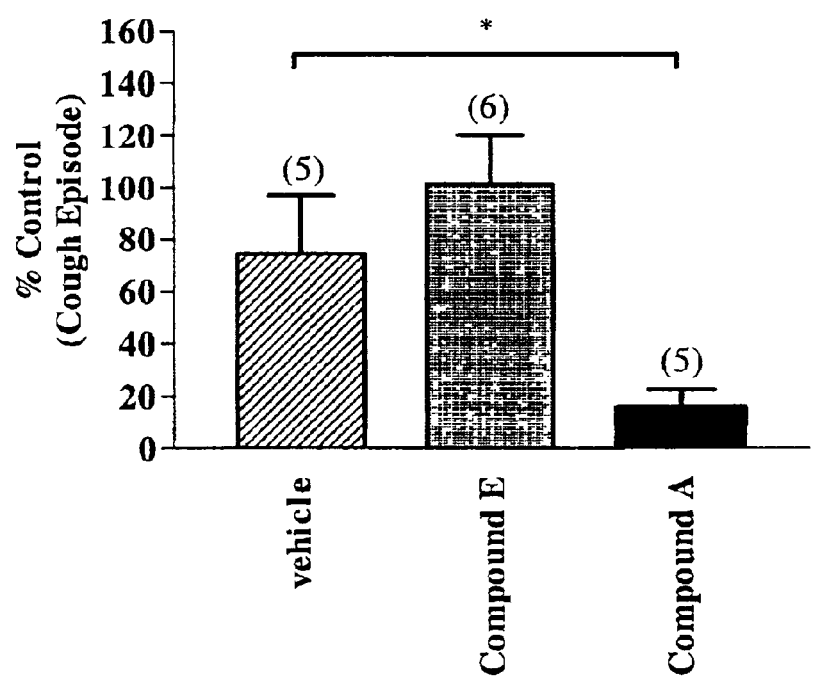
FIG. 5B shows the antitussive effects of compounds A and E administered orally (400 μmol/kg). The number of animals tested is indicated in the parenthesis. *P<0.05 and ***P<0.001 compared with the corresponding vehicle control. Normal saline was used as the vehicle for compounds C and A, and 5% Tween 80 in normal saline was used as the vehicle for compounds B and D, administered intraperitoneally; whereas, 5% Tween 80 in normal saline was used as the vehicle for compounds E and A, administered orally.
Figure 6:
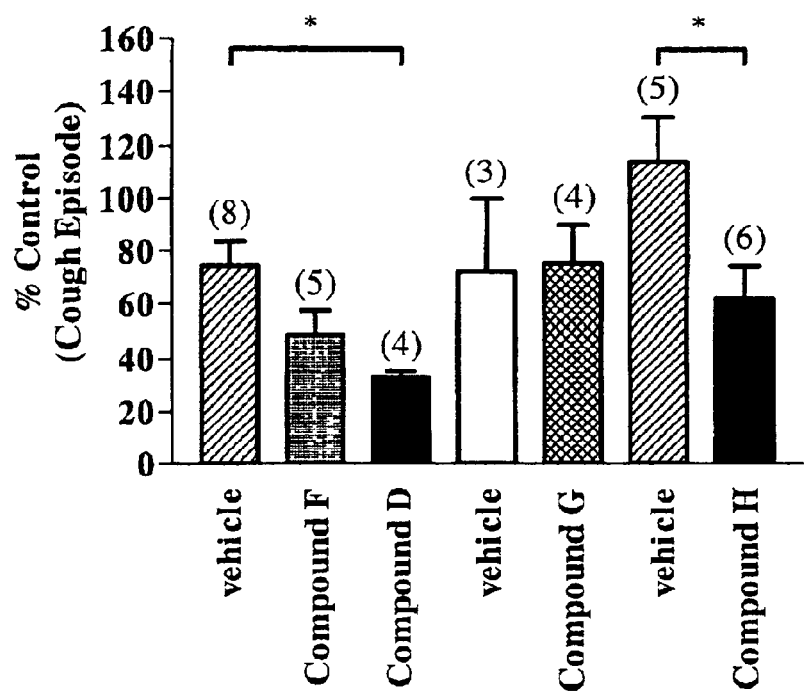
FIG. 6 illustrates the antitussive effects of compounds D, F, G and H administered intraperitoneally (133 μmol/kg). The number of animals tested is indicated in the parenthesis. *P<0.05 compared with the corresponding vehicle control. 5% Tween 80 in normal saline was used as the vehicle for compounds F, D and G, and normal saline was used as the vehicle for compound H.

The antitussive activities of the *Stemona* alkaloids, compounds B–H, were examined and their potencies were compared with that of compound A (see, FIG. 5). The results demonstrated that both compounds A and D significantly inhibited cough episodes in a dose-dependent manner. Compounds C, B, F and H exhibited marked reduction of cough episodes. Table 3 tabulates a structure-antitussive activity relationship of five naturally occurring *Stemona* alkaloids.

TABLE 3

Structure-antitussive activity relationship of five naturally occurring Stemona alkaloids

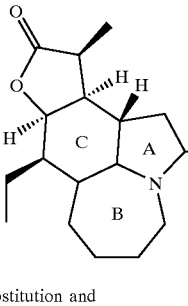

| Alkaloid | Substitution and Relative Configuration | | | No. of Animals | % Cough Episode (Composed with Vehicle Control) |
|---|---|---|---|---|---|
| | A/C | B/C | R | | |
| A | cis | cis |  | 5 | 21.7 ± 8.9 (po)* <br> 16.1 ± 7.3 (ip)*** |
| B | trans | cis | 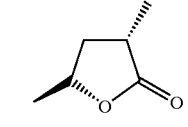 | 5 | 76.3 ± 14.7 (ip) |
| C | trans | trans | 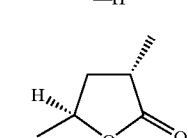 | 5 | 50.7 ± 16.6 (ip) |
| D | cis | cis | —H | 9 | 29.9 ± 8.3 (ip)*** |
| E | — | — | 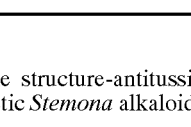 | 6 | 136.8 ± 25.6 (po) |

Table 4 tabulates the structure-antitussive activity relationship of three synthetic *Stemona* alkaloids and compound D.

TABLE 4

Structure-antitussive activity relationship of three synthetic Stemona alkaloids and compound D

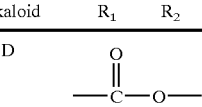

| Alkaloid | Substituted Group | | No. of Animals | % Cough Episode (Composed with Vehicle Control) |
|---|---|---|---|---|
| | $R_1$ | $R_2$ | | |
| D | 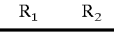 | | 9 | 29.9 ± 8.3 (ip)*** |

TABLE 4-continued

Structure-antitussive activity relationship of three synthetic Stemona alkaloids and compound D

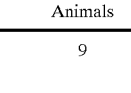

| Alkaloid | Substituted Group | | No. of Animals | % Cough Episode (Composed with Vehicle Control) |
|---|---|---|---|---|
| | $R_1$ | $R_2$ | | |
| F | —CH$_2$—OH | —OH | 5 | 62.2 ± 10.8 (ip) |
| G | —COOH | | 4 | 104.5 ± 20.4 (ip) |

TABLE 4-continued

Structure-antitussive activity relationship of three synthetic Stemona alkaloids and compound D

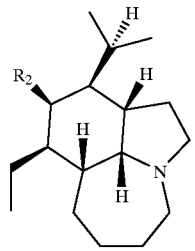

| Alkaloid | Substituted Group R$_1$ | R$_2$ | No. of Animals | % Cough Episode (Composed with Vehicle Control) |
|---|---|---|---|---|
| H | —CH$_2$—O— | —OH | 6 | 54.4 ± 10.6 (ip)* |

The rank order of antitussive potency was determined to be: compound A=D>C≈F≈H≈B. The results suggested that the defined tricyclic ring system (rings A, B and C) (FIG. 1) is the primary key structure contributing to the antitussive activity and all cis configurations at three ring junctions are the optimal structure. Furthermore, the substituted groups at 3 position on ring A and at 11 and 12 positions on ring C also affected the antitussive potency of these alkaloids and a α-methyl-γ-butyrolactone ring substitution in ring C produced the highest potency amongst all tested Stemona alkaloids.

Example 9

In Vivo Test for Determining the Mechanism of Antitussive Activity.

Figure 7:
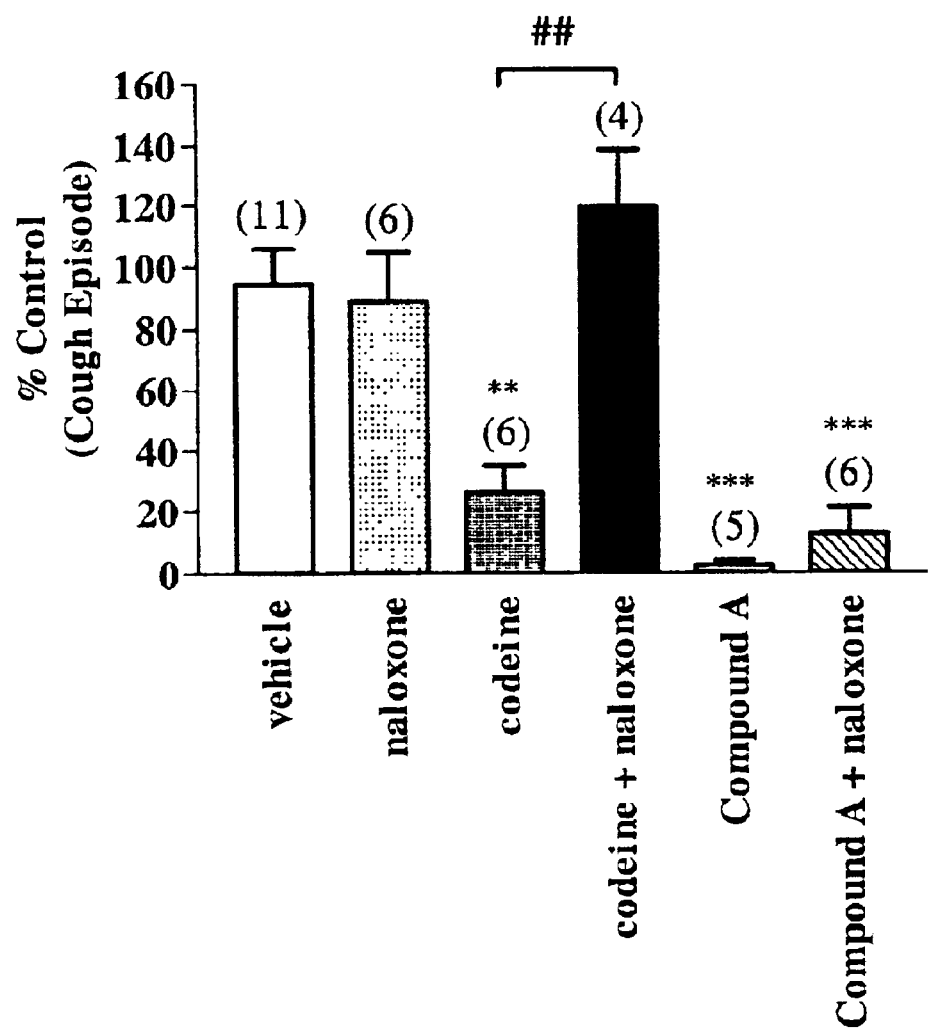
FIG. 7 illustrates the effect of naloxone (1 mg/kg) on the antitussive activity produced by neotuberostemonine (compound A, 100 mg/kg) and codeine (30 mg/kg). The number of animals tested is indicated in the parenthesis. P<0.01 and *P<0.001 compared with the vehicle control; and ##P<0.01 compared with the codeine treated group.

Further studies were conducted for the delineation of the mechanisms of antitussive activity produced by the representative Stemona alkaloid, compound A. Similarly, the sensitive animals were selected after the first citric acid challenge and allowed to recover for 24 hours. During the second challenge, animals were treated with a subcutaneous injection of different antagonists at different times prior to intraperitoneal administration of compound A (50 or 100 mg/kg). The antagonists examined included SCH 50911 (GABA$_B$ receptor antagonist) with a 40 min pretreatment at a dose of 10 mg/kg, WAY-100635 (5-HT$_{1A}$ receptor antagonist) with a 60 min pretreatment at a dose of 1 mg/kg, and haloperidol (Dopamine, D$_2$ receptor antagonist) with a 45 min pretreatment at a dose of 1 mg/kg. In addition, naloxone (nonselective opioid receptor antagonist) was administered subcutaneously at a dose of 5 mg/kg at 20 min after intraperitoneal administration of compound A (30 and 100 mg/kg). The effects of these antagonists on the antitussive activity of compound A were assessed by comparison of the changes in cough episodes and cough latency between animal groups administrated with compound A alone and concurrent administration of compound A and each antagonist tested. Furthermore, in a parallel study, the same treatment with naloxone was also conducted in the animals pretreated with intraperitoneal administration of codeine (30 mg/kg) for the positive control. The results indicated that all antagonists tested did not significantly affect the antitussive activity of Stemona alkaloids (FIG. 7, Table 5).

TABLE 5

Results of effects of different antagonists on the antitussive activity produced by compound A

| Antagonist | Receptor | % Antitussive Activity of Compound A |
|---|---|---|
| Naloxone | Opioid, (nonselective) | 86.51 ± 11.57 |
| SCH 50911 | GABA$_B$ | 83.25 ± 16.73 |
| WAY-100635 | 5-HT$_{1A}$ | 100.50 ± 1.67 |
| Haloperidol | Dopamine (D$_2$) | 115.21 ± 7.05 |

Example 10

In Vitro Receptor Binding Assays for Determining the Mechanism of Antitussive Activity The representative Stemona alkaloid, compound A, was subjected to the following primary receptor binding assays. The standard radiolabeled ligand binding experiments were performed at the concentration of 10 μM in duplicate by Novascreen Biosciences Crop. (7170 Standard Drive, Hanover, Md. 21076, USA). The tested receptors included all currently well-known receptors involved in producing the antitussive activity, for example, [$^3$H]Deltorphin (δ$_1$-opioid receptor), [$^3$H]Naltrindole (δ$_2$-opioid receptor), [$^3$H]DAMGO (μ-opioid receptor), [$^3$H]U69593 (κ$_1$-opioid receptor), [$^3$1H]CGP 54626A (GABA$_B$ receptor), [$^3$H]8-OH-DPAT (5HT$_{1A}$ receptor), and [3H]Glibenclamide (Dopamine D$_2$-receptor). In vitro receptor binding assays (Table 6) also demonstrated that neotuberostemonine did not show any affinity to all receptors examined. Therefore, the results obtained from both in vivo and in vitro studies confirmed that the antitussive activity of all five effective novel Stemona alkaloids and neotuberostemonine are not involved in opiate receptor pathways.

TABLE 6

Results of radiolabeled ligand binding assays of compound A

| Receptor | Source | Ligand | % Inhibition of Ligand Binding (average) | Affinity |
|---|---|---|---|---|
| Opioid, δ$_1$ | Rat forebrain | [$^3$H]Deltrophin | 5.95 | No |
| Opioid, δ$_2$ | Human recombinant | [$^3$H]Naltrindole | 8.32 | No |
| Opioid, κ | Guinea pig cerebellum | [$^3$H]U-69593 | 14.40 | No |
| Opioid, μ | Rat forebrain | [$^3$H]DAMGO | 7.37 | No |
| GABA$_B$ | Rat cortex | [$^3$H]CGP 54626A | 8.06 | No |
| 5-HT$_{1A}$ | Bovine hippocampus | [$^3$H]8-OH-DPAT | −18.42 | No |
| Dopamine, D$_2$ | Rate striatum | [$^3$H]Glibenclamide | 33.39 | ± |

The examples and embodiments described herein are for illustrative purposes only, and various modifications or changes thereof will be suggested to a person skilled in the art, and are included within the spirit and purview of this application and scope of the appended claims. All publications, patents, and patent applications cited herein are hereby incorporated by reference.

What is claimed is:

1. A compound having the formula:

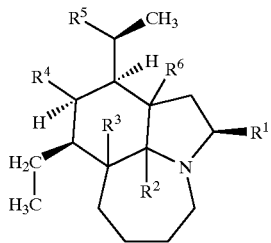

I wherein:
$R^1$ is a member selected from the group consisting of hydrogen and α(S)-methyl-γ(S)-butyroylactonyl;
$R^2$ is a member selected from the group consisting of β-oriented hydrogen and α-oriented hydrogen;
$R^3$ is a member selected from the group consisting of β-oriented hydrogen and α-oriented hydrogen;
$R^4$ is hydroxyl;
$R^5$ is a member selected from the group consisting of hydroxymethyl and carboxyl; and
$R^6$ is a member selected from the group consisting of β-oriented hydrogen and α-oriented hydrogen;
or alternatively,
$R^2$ is an α-oriented hydrogen, and
$R^4$ and $R^5$ together with the carbons to which they are attached, join to form a substituted γ(S)-butyroylactonyl or substituted furane ring;
or alternatively,
$R^1$ is hydrogen, and
$R^4$ and $R^5$ together with the carbons to which they are attached, join to form a substituted γ(S)-butyroylactonyl or substituted ring;
or alternatively,
$R^4$ and $R^5$ together with the carbons to which they are attached, join to form a substituted γ(S)-butyroylactonyl,
and $R^2$ and $R^6$ are both absent and form a pyrrole ring, provided however that when $R^1$ is α(S)-methyl-γ(R)-butyroylactonyl, $R^3$ is an α-oriented hydrogen.

2. The compound of claim 1, wherein said compound has the formula

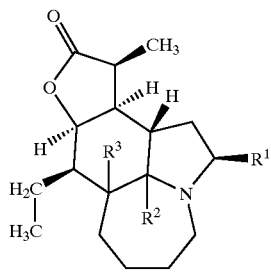

Ia wherein:
$R^1$ is hydrogen;
$R^2$ is a member selected from the group consisting of β-oriented hydrogen and α-oriented-hydrogen; and
$R^3$ is a member selected from the group consisting of β-oriented hydrogen and α-oriented hydrogen.

3. The compound of claim 1, wherein
$R^1$ is an α(S)-methyl-γ(S)-butyroylactonyl;
$R^2$ is an α-oriented hydrogen;
$R^3$ is an α-oriented hydrogen; and
$R^4$ and $R^5$ together with the carbons to which they are attached, join to form a substituted γ(S)-butyroylactonyl.

4. The compound of claim 1, wherein
$R^1$ is an α(S)-methyl-γ(S)-butyroylactonyl;
$R^2$ is an α-oriented hydrogen;
$R^3$ is a β-oriented hydrogen; and
$R^4$ and $R^5$ together with the carbons to which they are attached, join to form a substituted γ(S)-butyroylactonyl.

5. The compound of claim 2, wherein
$R^1$ is a hydrogen;
$R^2$ is a β-oriented hydrogen; and
$R^3$ is a β-oriented hydrogen.

6. The compound of claim 1, wherein said compound has the formula

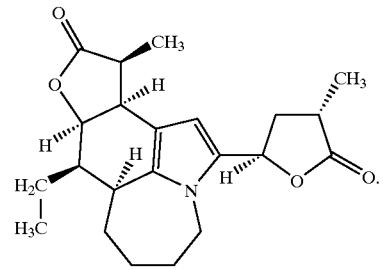

Ib

7. The compound of claim 1, wherein said compound has the formula

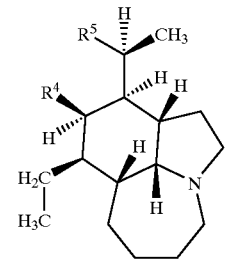

Ic wherein:
$R^4$ is a hydroxyl; and
$R^5$ is a member selected from the group consisting of hydroxymethyl and carboxyl;
or alternatively,
$R^4$ and $R^5$ together with the carbons to which they are attached, join to form a substituted furane ring.

8. The compound of claim 7, wherein
$R^4$ is a hydroxyl; and
$R^5$ is a hydroxymethyl.

9. The compound of claim 7, wherein
$R^4$ is a hydroxyl; and
$R^5$ is a carboxyl.

10. The compound of claim 7, wherein said compound has the formula

Id

11. A pharmaceutical composition, said composition comprising a compound having the formula:

I wherein:
R¹ is a member selected from the group consisting of hydrogen and α(S)-methyl-γ(S)-butyroylactonyl;
R² is a member selected from the group consisting of β-oriented hydrogen and α-oriented hydrogen;
R³ is a member selected from the group consisting of β-oriented hydrogen and α-oriented hydrogen;
R⁴ is hydroxyl;
R⁵ is a member selected from the group consisting of hydroxymethyl and carboxyl;
or alternatively,
R⁴ and R⁵ together with the carbons to which they are attached, join to form a substituted γ(S)-butyroylactonyl or substituted furane ring; and
R⁶ is a member selected from the group consisting of β-oriented hydrogen and α-oriented hydrogen;
or alternatively,
R⁴ and R⁵ together with the carbons to which they are attached, join to form a substituted γ(S)-butyroylactonyl,
and R² and R⁶ are both absent and form a pyrrole ring, provided however that when R¹ is α(S)-methyl-γ(R)-butyroylactonyl, R³ is an α-oriented hydrogen; and
a pharmaceutically acceptable carrier.

12. The composition of claim 11, wherein said compound has the formula

Ia wherein:
R¹ is a member selected from the group consisting of hydrogen and α(S)-methyl-γ(S)-butyroylactonyl;

R² is a member selected from the group consisting of β-oriented hydrogen and α-oriented hydrogen; and
R³ is a member selected from the group consisting of β-oriented hydrogen and α-oriented hydrogen.

13. The composition of claim 12, wherein
R¹ is an α(S)-methyl-γ(S)-butyroylactonyl;
R² is an α-oriented hydrogen; and
R³ is an α-oriented hydrogen.

14. The composition of claim 12, wherein
R¹ is an α(S)-methyl-γ(S)-butyroylactonyl;
R² is an α-oriented hydrogen; and
R³ is a β-oriented hydrogen.

15. The composition of claim 12, wherein
R¹ is a hydrogen;
R² is a β-oriented hydrogen; and
R³ is a β-oriented hydrogen.

16. The composition of claim 12, wherein
R¹ is an α(S)-methyl-γ(S)-butyroylactonyl;
R² is a β-oriented hydrogen; and
R³ is a β-oriented hydrogen.

17. The composition of claim 11, wherein said compound has the formula

Ib

18. The composition of claim 11, wherein said compound has the formula

Ic wherein:
R⁴ is a hydroxyl; and
R⁵ is a member selected from the group consisting of hydroxymethyl and carboxyl;
or alternatively,
R⁴ and R⁵ together with the carbons to which they are attached, join to form a substituted furane ring.

19. The composition of claim 18, wherein
R⁴ is a hydroxyl; and
R⁵ is a hydroxymethyl.

20. The composition of claim 18, wherein
R⁴ is a hydroxyl; and
R⁵ is a carboxyl.

21. The composition of claim 18, said compound has the formula

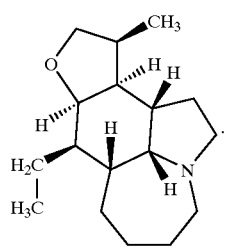

Id

22. A method for reducing coughing in a subject, said method comprising:
administering a pharmaceutically effective amount of a compound having the formula:

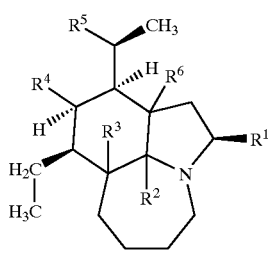

I wherein:
R¹ is a member selected from the group consisting of hydrogen and α(S)-methyl-γ(S)-butyroylactonyl;
R² is a member selected from the group consisting of β-oriented hydrogen and α-oriented hydrogen;
R³ is a member selected from the group consisting of β-oriented hydrogen and α-oriented hydrogen;
R⁴ is hydroxyl;
R⁵ is a member selected from the group consisting of hydroxymethyl and carboxyl;
or alternatively,
R⁴ and R⁵ together with the carbons to which they are attached, join to form a substituted γ(S)-butyroylactonyl or substituted furane ring; and
R⁶ is a member selected from the group consisting of β-oriented hydrogen and α-oriented hydrogen;
or alternatively,
R⁴ and R⁵ together with the carbons to which they are attached, join to form a substituted γ(S)-butyroylactonyl,
and R² and R⁶ are both absent and form a pyrrole ring, provided however that when R¹ is α(S)-methyl-γ(R)-butyroylactonyl, R³ is an α-oriented hydrogen.

23. The method of claim 22, wherein said compound has the formula

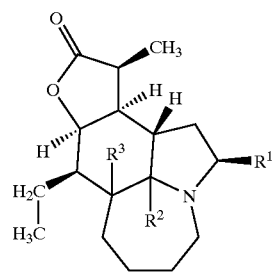

Ia wherein:
R¹ is a member selected from the group consisting of hydrogen and α(S)-methyl-γ(S)-butyroylactonyl;
R² is a member selected from the group consisting of β-orientated hydrogen and α-oriented hydrogen; and
R³ is a member selected from the group consisting of β-oriented hydrogen and α-oriented hydrogen.

24. The method of claim 23, wherein
R¹ is an α(S)-methyl-γ(S)-butyroylactonyl;
R² is an α-oriented hydrogen; and
R³ is an α-oriented hydrogen.

25. The method of claim 23, wherein
R¹ is an α(S)-methyl-γ(S)-butyroylactonyl;
R² is an α-oriented hydrogen; and
R³ is a β-oriented hydrogen.

26. The method of claim 23, wherein
R¹ is a hydrogen;
R² is a β-oriented hydrogen; and
R³ is a β-oriented hydrogen.

27. The method of claim 23, wherein
R¹ is an α(S)-methyl-γ(S)-butyroylactonyl;
R² is a β-orientated hydrogen; and
R³ is a β-oriented hydrogen.

28. The method of claim 22, wherein said compound has the formula

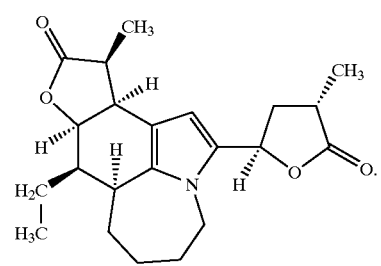

Ib

29. The method of claim 22, wherein said compound has the formula

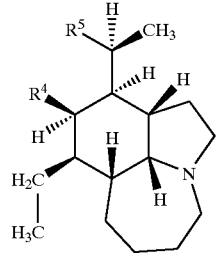

Ic wherein:
R⁴ is hydroxyl; and
R⁵ is a member selected from the group consisting of hydroxymethyl and carboxyl;
or alternatively,
R⁴ and R⁵ and the carbons to which they are attached join, to form a substituted furane ring.

30. The method of claim 29, wherein
R⁴ is a hydroxyl; and
R⁵ is a hydroxymethyl.

31. The method of claim 29, wherein
R⁴ is a hydroxyl; and
R⁵ is a carboxyl.

32. The method of claim 29, wherein said compound has the formula

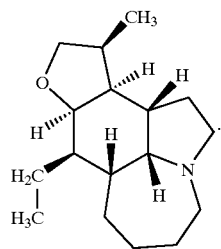

Id

* * * * *